(12) United States Patent
Hosoya et al.

(10) Patent No.: US 11,013,725 B2
(45) Date of Patent: May 25, 2021

(54) THERAPEUTIC AGENTS FOR INNER EAR HEARING IMPAIRMENT

(71) Applicant: Keio University, Tokyo (JP)

(72) Inventors: Makoto Hosoya, Tokyo (JP); Masato Fujioka, Tokyo (JP); Hideyuki Okano, Tokyo (JP); Kaoru Ogawa, Tokyo (JP); Tatsuo Matsunaga, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 15/654,267

(22) Filed: Jul. 19, 2017

(65) Prior Publication Data

US 2017/0333403 A1 Nov. 23, 2017

Related U.S. Application Data

(63) Continuation of application No. 15/544,419, filed as application No. PCT/JP2016/050861 on Jan. 13, 2016.

(30) Foreign Application Priority Data

Jan. 19, 2015 (JP) .............................. JP2015-007849

(51) Int. Cl.
*A61K 31/436* (2006.01)
*A61P 27/16* (2006.01)
(Continued)

(52) U.S. Cl.
CPC .......... *A61K 31/436* (2013.01); *A61K 31/155* (2013.01); *A61K 31/439* (2013.01);
(Continued)

(58) Field of Classification Search
None
See application file for complete search history.

(56) References Cited

U.S. PATENT DOCUMENTS

2004/0010002 A1 1/2004 Wasik et al.
2005/0095270 A1 5/2005 Staecker
(Continued)

FOREIGN PATENT DOCUMENTS

JP 1997-040581 A 2/1997
JP 2003-519655 A 6/2003
(Continued)

OTHER PUBLICATIONS

Op de Beecketal.; "Apoptosis in acquired and genetic hearing impairment: The programmed death of the hair cell"; 2011; Hear Res.; Nov. 2011; 281(1-2): 18-27. doi:10.1016/j.heares.2011.07.002 (Year: 2011).*

(Continued)

*Primary Examiner* — Timothy P Thomas
(74) *Attorney, Agent, or Firm* — Clark & Elbing LLP

(57) ABSTRACT

An object of the present invention is to provide novel apoptosis inhibitors and therapeutic agents for inner ear hearing impairment. As a pharmaceutical agent for this purpose, biguanide compounds represented by the following structural formula (I) or a rapamycin derivative represented by the following structural formula (II) as an active ingredient is provided:

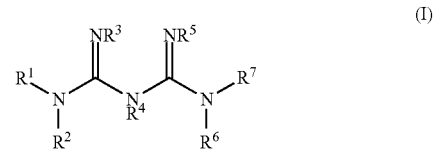

(I)

wherein $R^1$ to $R^7$ are each independently selected from a hydrogen atom, a halogen atom, or a $C_{1-6}$ alkyl group, a $C_{3-8}$ (Continued)

cycloalkyl group, a $C_{6-10}$ aryl group, a 5- or 6-membered heteroaryl group, or a 5- or 6-membered non-aromatic heterocyclic group, each of which may have a substituent selected from a halogen atom, a cyano group, a $C_{1-6}$ alkyl group, a $C_{1-6}$ alkoxy group, a $C_{1-6}$ alkoxy carbonyl group, a $C_{3-8}$ cycloalkyl group, a $C_{2-6}$ alkenyl group, a $C_{2-6}$ alkynyl group, and a phenyl group;

(II)

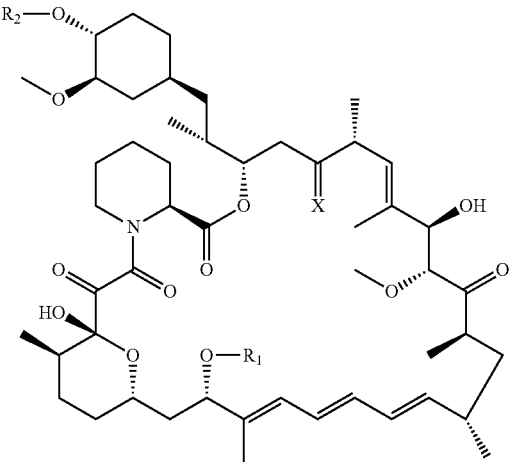

wherein $R_1$ is a $C_{1-6}$ alkyl or a $C_{3-6}$ alkynyl, $R_2$ is H, —CH2-OH or —$CH_2$—$CH_2$—OH, and X is =O, (H, H) or (H, OH).

2 Claims, 14 Drawing Sheets

(51) Int. Cl.
 *A61K 31/155* (2006.01)
 *A61K 31/439* (2006.01)
 *G01N 33/50* (2006.01)

(52) U.S. Cl.
 CPC .......... *A61P 27/16* (2018.01); *G01N 33/5044* (2013.01); *G01N 2510/00* (2013.01)

(56) References Cited

U.S. PATENT DOCUMENTS

| | | |
|---|---|---|
| 2008/0221102 A1 | 9/2008 | Hangauer et al. |
| 2010/0016218 A1 | 1/2010 | Lichter et al. |
| 2010/0087474 A1 | 4/2010 | Kaushal et al. |
| 2010/0260733 A1 | 10/2010 | Qi |
| 2012/0071349 A1 | 3/2012 | Qi |
| 2016/0199446 A1 | 7/2016 | Lichter et al. |
| 2017/0027914 A1 | 2/2017 | Qi |
| 2019/0298799 A1 | 10/2019 | Lichter et al. |

FOREIGN PATENT DOCUMENTS

| | | | |
|---|---|---|---|
| JP | 2004-99537 A | 4/2004 | |
| JP | 2004-123713 A | 4/2004 | |
| JP | 2008-539276 A | 11/2008 | |
| JP | 2010-527361 A | 8/2010 | |
| WO | WO-2005/009287 A2 | 2/2005 | |
| WO | WO-2008022256 A2 * | 2/2008 | ........... A61K 31/192 |
| WO | WO-2010/118419 A2 | 10/2010 | |

OTHER PUBLICATIONS

Fang et al.; "Rapamycin alleviates cisplatin-induced ototoxicity in vivo"; 2014; Biochemical and Biophysical Research Communications 448: 443-447 (Year: 2014).*
Dallos et al.; "Prestin and the cochlear amplifier"; 2006; J Physiol 576.1 (2006) pp. 37-42 (Year: 2006).*
Rotman-Pikielny, et al.; "Retention of pendrin in the endoplasmic reticulum is a major mechanism for Pendred syndrome"; 2002; Human Molecular Genetics; 11(21): 2625-2633 (Year: 2002).*
Menendez-Benito et al.; "Endoplasmic reticulum stress compromises the ubiquitin-proteasome system"; 2005; Human Molecular Genetics; 14(19): 2787-2799; doi: 10.1093/hmg/ddi312 (Year: 2005).*
Nixon; "The role of autophagy in neurodegenerative disease"; 2013; Nature Medicine 19(8): 983-997; doi:10.1038/nm.3232 (Year: 2013).*
Wu et al.; "Rapamycin Upregulates Autophagy by Inhibiting the mTOR-ULK1 Pathway, Resulting in Reduced Podocyte Injury"; PLoS ONE 8(5): e63799; pp. 1-10; doi:10.1371/journal.pone.0063799 (Year: 2013).*
He et al., "Rapamycin inhibits acrolein-induced apoptosis by alleviating ROS-driven mitochondrial dysfunction in male germ cells," Cell Prolif. 47(2):161-71 (2014).
Op de Beeck et al., "Apoptosis in acquired and genetic hearing impairment: the programmed death of the hair cell," Hear Res. 281(1-2):18-27 (2011).
Extended European Search Report for European Patent Application No. 17187312.8, dated Feb. 16, 2018 (9 pages).
Conde de la Rosa et al., "Oxidative stress induced apoptosis is inhibited by metformin via an ERK and Src dependent pathway in rat hepatocytes," European Journal of Gastroenterology & Hepatology 18(1):A50-A51 (2006) (4 pages).
Fang et al., "Rapamycin alleviates cisplatin-induced ototoxicity in vivo," Biochem Biophys Res Commun. 448(4):443-7 (2014).
Glutz et al., "Metformin Protects Auditory Hair Cells from Gentamicin-Induced Toxicity in vitro," Audiology & Neurotology 20(6):360-369 (2015) (12 pages).
Harris et al., "Prevention of noise-induced hearing loss with Src-PTK inhibitors," Hear Res. 208(1-2):14-25 (2005).
Hayashi et al., "Molecular crosstalk between Nrf2/Keap I signaling pathway, autophagy and necrosis in auditory cells," Otolaryngology—Head and Neck Surgery 145(2):221 (2011).
Jung et al., "Protective role of antidiabetic drug metformin against gentamicin induced apoptosis in auditory cell line," Hear Res. 282(1-2):92-6 (2011).
Leclerc et al., "Metformin induces apoptosis through AMPK-dependent inhibition of UPR signaling in ALL lymphoblasts," PLoS One. 8(8):e74420 (2013) (10 pages).
Leitmeyer et al., "Inhibition of mTOR by rapamycin results in auditory hair cell damage and decreased spiral ganglion neuron outgrowth and neurite formation In Vitro," BioMed Research International 21(2):1-10 (2015).
Oishi et al., "Metformin protects against gentamicin-induced hair cell death in vitro but not ototoxicity in vivo," available in PMC Nov. 7, 2015, published in final edited form as: Neurosci Lett. 583:65-9 (2014) (13 pages).
Woltman et al., "Rapamycin induces apoptosis in monocyte- and CD34-derived dendritic cells but not in monocytes and macrophages," Blood 98(1):174-80 (2001).
Final Office Action for U.S. Appl. No. 15/544,419 dated Jan. 17, 2019 (19 pages).
Gillespie, "Sensory Organ Disorders (Retina, Auditory, Olfactory, Gustatory)" in Neural Circuit Development and Function in the Brain, 2013; https://www.sciencedirect.com/topics/medicine-and-dentistry/pendred-syndrome (2013) (3 pages).
MeSH entry for Pendred syndrome, https://www.ncbi.nlm.nih.gov/mesh/?term=pendred+syndrome; accessed Jan. 10, 2019 (2019) (1 page).
Senou et al. "A coherent organization of differentiation proteins is required to maintain an appropriate thyroid function in the Pendred thyroid," J Clin Endocrinol Metab. 95:4021-4030 (2010).
Extended European Search Report for European Patent Application No. 16740038.1 dated Sep. 7, 2018 (10 pages).

(56) References Cited

OTHER PUBLICATIONS

Lee et al., "Protective effect of metformin on gentamicin-induced vestibulotoxicity in rat primary cell culture," Clin Exp Otorhinolaryngol. 7(4):286-94 (2014).

Non-Final Office Action for U.S. Appl. No. 15/544,419, dated May 1, 2018 (14 pages).

Mujica-Mota et al., "Safety and otoprotection of metformin in radiation-induced sensorineural hearing loss in the guinea pig," Otolaryngology-Head and Neck Surgery 150(5):859-865 (2014).

Nixon, "The role of autophagy in neurodegenerative disease," Nat Med. 19(8)983-97 (2013).

Non-Final Office Action for U.S. Appl. No. 15/544,419, dated Aug. 23, 2019 (14 pages).

Rotman-Pikielny et al., "Retention of pendrin in the endoplasmic reticulum is a major mechanism for Pendred syndrome," Hum Mol Genet. 11(21):2625-33 (2002).

Menéndez-Benito et al., "Endoplasmic reticulum stress compromises the ubiquitin-proteasome system," Hum Mol Genet. 14(19):2787-99 (2005).

Tomic et al., "Metformin inhibits melanoma development through autophagy and apoptosis mechanisms," Cell Death Dis. 2:e199 (2011) (10 pages).

Quentin et al., "Metformin differentially activates ER stress signaling pathways without inducing apoptosis," Dis Model Mech. 5(2):259-69 (2012).

Hosoya et al., "Cochlear Cell Modeling Using Disease-Specific iPSCs Unveils a Degenerative Phenotype and Suggests Treatments for Congenital Progressive Hearing Loss," Cell Reports 18:68-81 (2017).

Szegezdi et al., "Mediators of endoplasmic reticulum stress-induced apoptosis," EMBO Reports 7(6):880-885 (2006).

Final Office Action for U.S. Appl. No. 15/544,419 dated Jun. 1, 2020 (21 pages).

Mount et al., "The SLC26 gene family of multifunctional anion exchangers," Pflugers Arch. 447(5):710-21 (2004).

Royaux et al., "Localization and functional studies of pendrin in the mouse inner ear provide insight about the etiology of deafness in pendred syndrome," J Assoc Res Otolaryngol. 4(3):394-404 (2003).

Taylor et al., "Mutations of the PDS gene, encoding pendrin, are associated with protein mislocalization and loss of iodide efflux: implications for thyroid dysfunction in Pendred syndrome," J Clin Endocrinol Metab. 87(4):1778-84 (2002).

Wangemann, "The role of pendrin in the development of the murine inner ear," Cell Physiol Biochem. 28(3):527-34 (2011).

Zdebik et al., "Potassium ion movement in the inner ear: insights from genetic disease and mouse models," Physiology (Bethesda). 24:307-16 (2009).

Ravikumar et al., "Rapamycin pre-treatment protects against apoptosis," Hum Mol Genet. 15(7):1209-16 (2006).

* cited by examiner (A)

(B)

NEW SHEET

THERAPEUTIC AGENTS FOR INNER EAR HEARING IMPAIRMENT

CROSS REFERENCE TO RELATED DOCUMENTS

This application claims the benefit of Japanese Patent Application No. 2015-007849 filed on Jan. 19, 2015, the entire disclosure of which is hereby incorporated by reference.

TECHNICAL FIELD

The present invention relates to therapeutic agents for inner ear hearing impairment.

BACKGROUND ART

In the inner ear, hair cells and spiral ganglion cells in the cochlea play an important role in hearing. Due to the lack of regenerative potential of these cells, no therapeutic effect can be expected after their loss. For this reason, it is considered that treatment of hearing impairment with medicament is difficult.

Accordingly, therapeutic agents currently used for hearing impairment are, at best, circulation enhancers and anti-inflammatory agents for sudden sensorineural hearing impairment caused by circulation disorders and/or inflammation of the inner ear (JP-A-2004-123713), and development of other medicament for hearing impairment is thus expected.

SUMMARY OF INVENTION

Problems to be Solved by the Invention

The present invention was made with an object of providing novel apoptosis inhibitors and therapeutic agents for inner ear hearing impairment.

Means to Solve the Problem

An aspect of the present invention is a pharmaceutical agent for treating inner ear hearing impairment resulted from apoptosis containing, as an active ingredient, a biguanide compound represented by the following formula I or a rapamycin derivative represented by the following formula II. The inner ear hearing impairment resulted from apoptosis may be the one caused by Pendred syndrome. The biguanide compound may be metformin. The rapamycin derivative may be rapamycin.

A further aspect of the present invention is an apoptosis inhibitor containing, as an active ingredient, a biguanide compound represented by the following formula I or a rapamycin derivative represented by the following formula II. The apoptosis inhibitor may be the one that inhibits apoptosis of inner ear cells. The biguanide compound may be metformin. The rapamycin derivative may be rapamycin.

A further aspect of the present invention is a method of examining apoptosis including the steps of administering a compound represented by the following structural formula (I) or (II) in vitro to an inner ear cell; inducing apoptosis in the inner ear cell; and examining the apoptosis induced in the inner ear cell.

A further aspect of the present invention is a method of screening compounds represented by the following structural formula (I) or (II) for a substance inhibiting apoptosis, including the steps of administering the compounds represented by the following structural formula (I) or (II) in vitro to inner ear cells; inducing apoptosis in the inner ear cells; and examining the apoptosis induced in the inner ear cells.

A further aspect of the present invention is a method of screening compounds represented by the following structural formula (I) or (II) for a pharmaceutical agent for treating inner ear hearing impairment resulted from apoptosis, including the steps of administering the compounds represented by the following structural formula (I) or (II) in vitro to inner ear cells; inducing apoptosis in the inner ear cells; and examining the apoptosis induced in the inner ear cells.

A further aspect of the present invention is a method of treating a patient with inner ear hearing impairment resulted from apoptosis, including the step of administering an effective amount of a biguanide compound represented by the following formula I or a rapamycin derivative represented by the following formula II to the patient. The biguanide compound or the rapamycin derivative may be administered into a tympanic cavity. The inner ear hearing impairment resulted from apoptosis may be caused by Pendred syndrome. The biguanide compound may be metformin. The rapamycin derivative may be rapamycin.

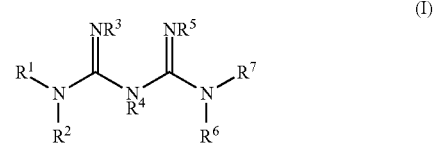

wherein $R^1$ to $R^7$ are each independently selected from a hydrogen atom, a halogen atom, or a $C_{1-6}$ alkyl group, a $C_{3-8}$ cycloalkyl group, a $C_{6-10}$ aryl group, a 5- or 6-membered heteroaryl group, or a 5- or 6-membered non-aromatic heterocyclic group, each of which may have a substituent selected from a halogen atom, a cyano group, a $C_{1-6}$ alkyl group, a $C_{1-6}$ alkoxy group, a $C_{1-6}$ alkoxy carbonyl group, a $C_{3-8}$ cycloalkyl group, a $C_{2-6}$ alkenyl group, a $C_{2-6}$ alkynyl group, and a phenyl group

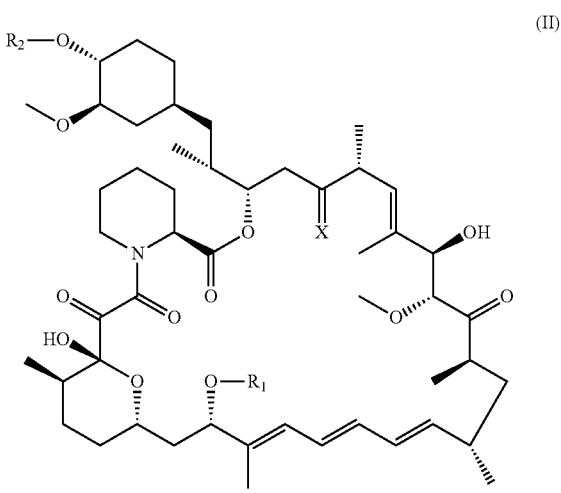

wherein $R_1$ is a $C_{1-6}$ alkyl or a $C_{3-6}$ alkynyl, $R_2$ is H, —CH2-OH or —$CH_2$—$CH_2$—OH, and X is =O, (H, H) or (H, OH)

EMBODIMENTS FOR CARRYING OUT THE INVENTION

Figure 1:
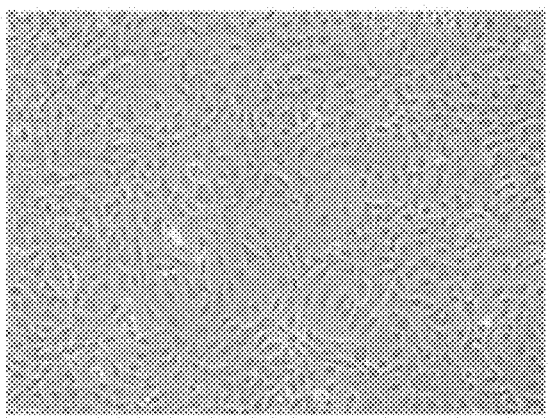
FIG. 1 (A) Phase contrast micrograph of inner ear stem cells obtained in one embodiment of the present invention and (B) micrographs of the inner ear stem cells stained with (a) anti-PAX 2 antibody, (b) anti-PAX 8 antibody, and (c) anti-SOX2 antibody in an embodiment of the present invention.
Figure 1:
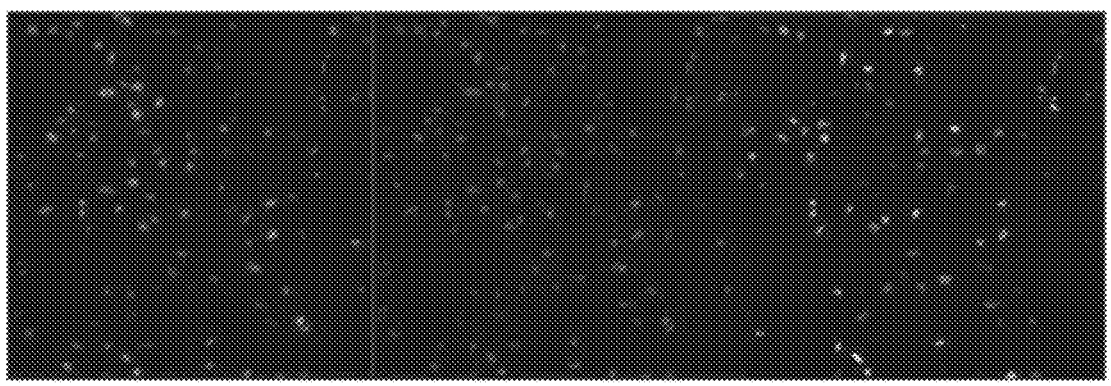

Hereinafter, embodiments of the present invention completed based on the above findings will be described in detail with reference to examples. The objects, features, advantages, and ideas of the present invention are apparent to those skilled in the art from the description of this specification. Furthermore, those skilled in the art can easily reproduce the present invention from the description herein. The embodiments and specific examples described below represent preferable embodiments of the present invention, which are given for the purpose of illustration or explanation. The present invention is not limited thereto. It is obvious to those skilled in the art that various changes and modifications may be made according to the description of the present specification within the spirit and scope of the present invention disclosed herein.

(1) Apoptosis Inhibitors

An embodiment of the present invention is an apoptosis inhibitor for inner ear cells containing, as an active ingredient, a biguanide compound (shown as the following structural formula I) or a rapamycin derivative (shown as the following structural formula II) or a pharmaceutically acceptable salt thereof.

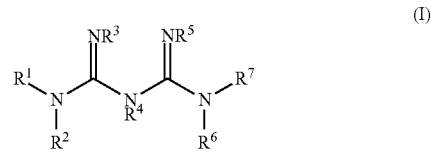

wherein $R^1$ to $R^7$ are each independently selected from a hydrogen atom, a halogen atom, or a $C_{1-6}$ alkyl group, a $C_{3-8}$ cycloalkyl group, a $C_{6-10}$ aryl group, a 5- or 6-membered heteroaryl group, or a 5- or 6-membered non-aromatic heterocyclic group, each of which may have a substituent selected from a halogen atom, a cyano group, a $C_{1-6}$ alkyl group, a $C_{1-6}$ alkoxy group, a $C_{1-6}$ alkoxy carbonyl group, a $C_{3-8}$ cycloalkyl group, a $C_{2-6}$ alkenyl group, a $C_{2-6}$ alkynyl group, and a phenyl group.

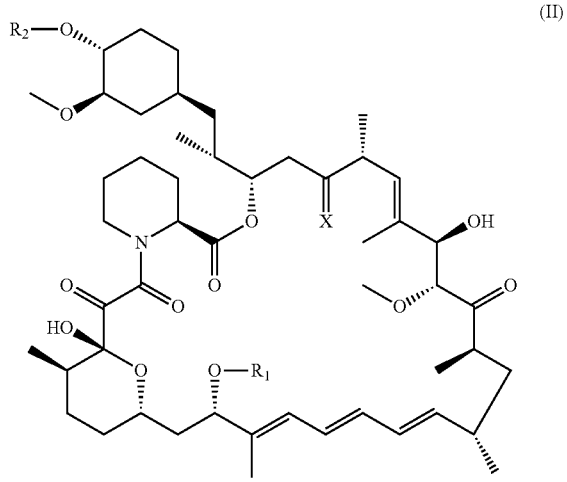

(II)

wherein $R_1$ is a $C_{1-6}$ alkyl or a $C_{3-6}$ alkynyl, $R_2$ is H, —CH2-OH or —CH$_2$—CH$_2$—OH, and X is =O, (H, H) or (H, OH).

Inner ear cells to be protected from apoptosis are not particularly limited, but those susceptible to apoptosis are preferable and those derived from an animal suffered from inner ear hearing impairment resulted from apoptosis are more preferable. Inner ear hearing impairment is not particularly limited as long as it is resulted from apoptosis, and examples include hearing impairment in Pendred syndrome and presbycusis. Furthermore, the inner ear cells to be protected from apoptosis may be those existing in a body of an organism or cultured cells. Species of the organism are not particularly limited, but vertebrates are preferable, and human is most preferable. The cultured cells may be established cell lines, primary culture cells, or inner ear cells which have differentiated from stem cells. Details of how to induce differentiation of stem cells into inner ear cells will be described later.

As described above, the apoptosis inhibitors of the present invention can be used for inner ear cells, and thus are useful as pharmaceutical agents for treating inner ear hearing impairment resulted from apoptosis. The inner ear hearing impairment to be treated is not particularly limited as long as it is inner ear hearing impairment resulted from apoptosis, and examples include hearing impairment in Pendred syndrome and presbycusis. The term "treatment" as used herein includes improvement of the aforementioned hearing impairment, prevention of progression of the aforementioned hearing impairment and prevention of the aforementioned hearing impairment.

(2) Biguanide Compounds

Biguanide is a compound composed of two guanidine molecules joined by a common nitrogen and has the following structure (III).

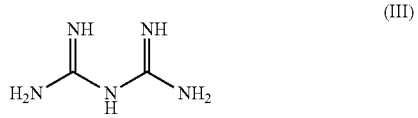

(III)

In this specification, a biguanide compound collectively refers to biguanides and substituted biguanides. The substituent is not particularly limited and examples include a hydrogen atom, a halogen atom, $C_{1-6}$ alkyl groups, $C_{3-8}$ cycloalkyl groups, $C_{6-10}$ aryl groups, 5- or 6-membered heteroaryl groups, 5- or 6-membered non-aromatic heterocyclic groups, wherein the $C_{1-6}$ alkyl groups, $C_{3-8}$ cycloalkyl groups, $C_{6-10}$ aryl groups, 5- or 6-membered heteroaryl groups, and 5- or 6-membered non-aromatic heterocyclic groups may have a substituent selected from a halogen atom, a cyano group, a $C_{1-6}$ alkyl group, a $C_{1-6}$ alkoxy group, a $C_{1-6}$ alkoxy carbonyl group, a $C_{3-8}$ cycloalkyl group, a $C_{2-6}$ alkenyl group, a $C_{2-6}$ alkynyl group, and a phenyl group. That is, the biguanide compounds include the compound represented by the following structural formula.

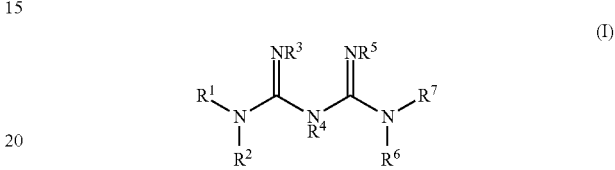

(I)

wherein $R^1$ to $R^7$ are each independently selected from a hydrogen atom, a halogen atom, or a $C_{1-6}$ alkyl group, a $C_{3-8}$ cycloalkyl group, a $C_{6-10}$ aryl group, a 5- or 6-membered heteroaryl group, or a 5- or 6-membered non-aromatic heterocyclic group, each of which may have a substituent selected from a halogen atom, a cyano group, a $C_{1-6}$ alkyl group, a $C_{1-6}$ alkoxy group, a $C_{1-6}$ alkoxy carbonyl group, a $C_{3-8}$ cycloalkyl group, a $C_{2-6}$ alkenyl group, a $C_{2-6}$ alkynyl group, and a phenyl group, but not all of $R^1$ to $R^7$ are hydrogen.

The most preferable compound is metformin having the following structural formula IV.

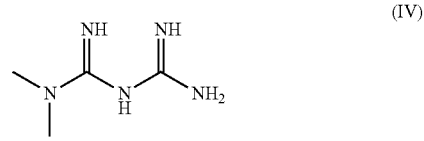

(IV)

(3) Rapamycin Derivatives

Rapamycin is a compound having the following structural formula V.

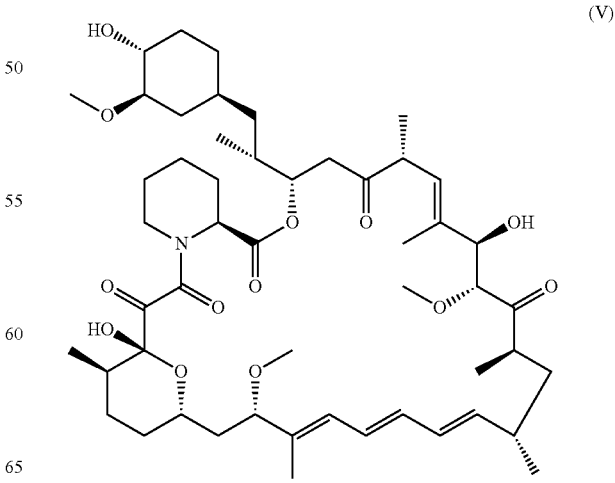

(V)

In the present specification, rapamycin derivatives include compounds represented by the following structural formula.

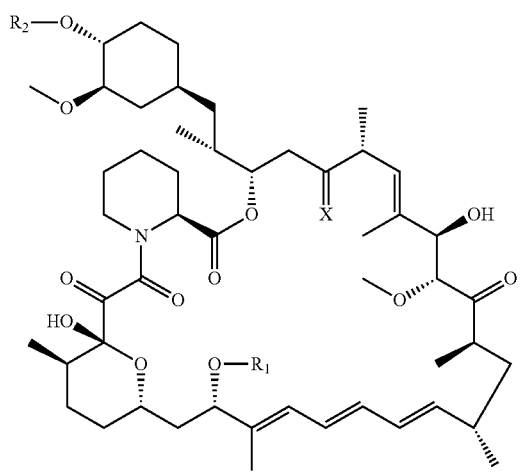

(II)

wherein $R_1$ is a $C_{1-6}$ alkyl or a $C_{3-6}$ alkynyl, $R_2$ is H, —CH2-OH or —CH$_2$—CH$_2$—OH, and X is =O, (H, H) or (H, OH).

For example, the rapamycin derivatives include (1) 40-O-substituted rapamycin derivatives (e.g., 40-O-alkyl-rapamycin derivatives such as 40-O-hydroxyalkyl-rapamycin derivatives and 40-O-(2-hydroxy)-ethyl-rapamycin), (2) 32-deoxo-rapamycin and derivatives thereof and 32-hydroxy-rapamycin and derivatives thereof, (3) 16-O-substituted rapamycin derivatives (e.g., 16-pent-2-ynyloxy-32-deoxorapamycin, 16-deoxo-32(S or R)-dihydro-rapamycin, and 16-deoxo-32(S or R)-dihydro-40-O-(2-hydroxyethyl)-rapamycin), (4) rapamycin derivatives having an acyl substituent at the oxygen at the 40-position (e.g., 40-[3-hydroxy-2-(hydroxymethyl)-2-methylpropanoate]-rapamycin (also known as CCI-779)), (5) rapamycin derivatives substituted with heterocyclyl at the 40-position (e.g., 40-epi-(tetrazolyl)-rapamycin (also known as ABT-578)), (6) so-called rapalogs described in, for example, WO9802441 or WO0114387 (e.g., 40-O-phospho-containing rapamycin derivatives (such as 40-O-dimethylphosphinyl-rapamycin (including AP23573))), and (7) 40-O-alkoxy-alkyl-rapamycin derivatives (e.g., compounds disclosed under the trade name Biolimus (including compounds disclosed as Biolimus A9 (40-O-(2-ethoxy)-ethyl-rapamycin) and compounds disclosed under the trade names TAFA-93, AP23464, AP23675 or AP23841), but (8) rapamycin is the most preferable.

(4) Induction of Differentiation of Stem Cells Into Inner Ear Cells

A method of inducing differentiation of stem cells into inner ear cells (hereinafter, also referred to as an inner ear cell induction method) is described now. Stem cells are not particularly limited, but pluripotent stem cells and inner ear stem cells can be exemplified. The inner ear cell induction method is described in detail using pluripotent stem cells as an example.

Figure 15:
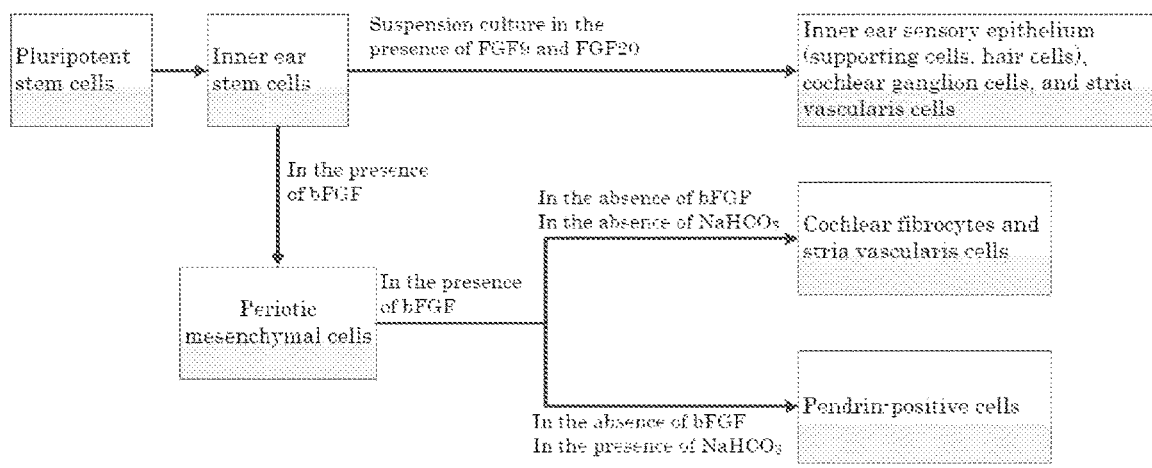
FIG. 15 Schematic diagram of an exemplary procedure for an inner ear cell induction method.

This inner ear cell induction method can be performed as shown in FIG. 15 and as outlined below:

[1] Induction of Differentiation of Pluripotent Stem Cells into Inner Ear Stem Cells In a induction method from pluripotent stem cells to inner ear stem cells, the following steps are performed in this order:

First step: culturing pluripotent stem cells in the presence of a ROCK inhibitor;
Second step: culturing the cells in the absence of ROCK inhibitor;
Third step: culturing the cells in a serum-free medium;
Fourth step: culturing the cells in a serum-free medium containing a growth factor; an
Fifth step: dissociating the cells into single cells.

Other step(s) not essential for this method can be added between individual steps.

The pluripotent stem cells are not particularly limited as long as they have pluripotent differentiation potential (i.e., multipotency or pluripotency) and examples include embryonic stem cells (ES cells), induced pluripotent stem cells (iPS cells), and Muse cells. Cells with totipotency are particularly preferable.

The ROCK (Rho-associated coiled-coil forming kinase/Rho-associated kinase) inhibitor is not particularly limited and examples include Y-27632, Fasudil hydrochloride, K-115 (Ripasudil hydrochloride hydrate), and DE-104. The optimal concentration of the ROCK inhibitor can easily be determined as appropriate, but 0.05% to 0.2% is preferable and 0.1% is more preferable.

The medium used in the first and second steps is not particularly limited as long as pluripotent stem cells can be kept therein and mTeSR1 is an example. The first step is performed preferably for 1 to 3 days, and more preferably for 1 to 2 days. The second step is performed preferably for 1 to 3 days, and more preferably for 1 to 2 days.

In the second step, what the term "in the absence of ROCK inhibitor" means is that a ROCK inhibitor is substantially absent and may be contained at a concentration at which no effect is observed.

Examples of the serum-free medium used in the third step include DMEM/F12+B27+N2+GlutaMax+Nonessential amino acid. In the third step, the cells are cultured preferably for 2 to 6 days, more preferably for 2 to 4 days and most preferably for 3 days.

Examples of the serum-free medium used in the fourth step include DMEM/F12+B27+N2+GlutaMax+Nonessential amino acid, but it is preferable that the same serum-free medium as in the third step is used. For the growth factor, at least one selected from the group consisting of bFGF, FGF3, FGF10, and FGF19 may be added, but it is preferable that all of them are added. Preferable concentrations of them are 10 to 50 ng/ml, 10 to 50 ng/ml, 10 to 50 ng/ml, and 10 to 50 ng/ml, respectively. Furthermore, it is preferable that the cells are cultured in the presence of BMP4 at the earlier stage of the culture and in the absence of BMP4 at the latter stage. The concentration of BMP4 to be added at the earlier stage is preferably 5 to 50 ng/ml. For the culture at the latter stage, the term "in the absence of BMP4" means that the BMP4 is substantially absent and may be contained at a concentration at which no effect is observed. The cells at the earlier stage are cultured preferably for 2 to 6 days, more preferably for 2 to 4 days, and most preferably for 3 days. The cells at the latter stage are cultured preferably for 2 to 6 days, more preferably for 2 to 4 days, and most preferably for 3 days. The inner ear stem cells thus obtained have differentiation potential to inner ear stem cells.

As the fifth step, spheres of the cells obtained in the fourth step are dissociated into single cells. The method of dissociating spheres into single cells is not particularly limited and, for example, trypsin or Accutase can be used. It is preferable that after the cells are dissociated with an enzyme or by mechanical means such as pipetting, the dissociated single cells are selected and the residual clumps of cells are removed, using, for example, a nylon mesh to remove undifferentiated cells or clumps.

To culture inner ear stem cells, using culture dishes coated with a coating agent, the cells are cultured under a hypoxic condition to maintain their stem cell ability (the sixth step). The coating agent used is not particularly limited but poly-O-fibronectine is the most preferable. The stem cells to be cultured may be either those obtained in the fourth step or those obtained in the fifth step. Examples of medium supplemented with serum used in this step include DMEM and F12 but DMEM/F12 containing N2 and B27 in addition to the serum (e.g., FBS) is the most preferable. The concentration of oxygen in the hypoxic condition in this step is preferably 4% to 10%, more preferably 4% to 6%, and most preferably 4%. At least one growth factor selected from the group consisting of bFGF, EGF, and IGF1 may be added to the culture medium, but it is preferable that all of them are added. Their preferable concentrations are 10 to 30 ng/ml, 10 to 30 ng/ml, and 10 to 50 ng/ml, respectively.

[2] Induction of Differentiation of Inner Ear Stem Cells Into Inner Ear Sensory Epithelium Such as Supporting Cells and Hair Cells, Cochlear Ganglion Cells and Stria Vascularis Cells In a method of inducing inner ear stem cells into inner ear sensory epithelium, cochlear ganglion cells and stria vascularis cells, the following steps are performed in this order:

First step: culturing inner ear stem cells in suspension; and

Second step: culturing the cells in the presence of FGF9 and FGF20.

Other steps not essential for this method can be added between the steps.

In the first step, inner ear stem cells are cultured in suspension. Specifically, as in the fifth step, the inner ear stem cells are dissociated into single cells. The dissociated cells are then cultured in suspension; for this purpose, dishes for suspension culture with which cells can be cultured in non-adherent conditions are used. For example, dishes for non-adherent culture such as plastic dishes for bacterial culture may be used. The term "suspension culture" or "culture in suspension" means that target cells or spheres are cultured without being adhered to the bottom surface of a culture vessel, and the term "adherent culture" or "culture on a substrate" means that the target cells or spheres are cultured with being adhered to the bottom surface of a culture vessel. The expression that cells or speheres adhere to the bottom surface of a culture vessel during culture means that the cells or spheres are settled on the bottom surface of the culture vessel through cell-substrate adhesion molecules contained in, for example, an extracellular matrix (ECM) and refers to that cells or spheres don't float up in the culture liquid even when the culture liquid is shaked gently. On the other hand, the expression that cells or spheres do not adhere to the bottom surface of a culture vessel during culture means that the cells or spheres are not settled on the bottom surface of the culture vessel through cell-substrate adhesion molecules contained in, for example, ECM and refers to that cells or spheres float up in the culture liquid when the culture liquid is shaked gently even if they are in contact with the bottom surface. For adherent culture, it is preferable to chemically treat or coat, with a coating agent (e.g., gelatin, polylysine, or agar) that promotes adhesion, the bottom surface of plastic dishes, in order to promote adhesion of cells to a substrate. For suspension culture, it is preferable that the bottom surface of plastic dishes is not treated or is coated with a coating agent for preventing adhesion (e.g., poly(2-hydroxyethyl methacrylate)) to prevent the cells from adhering to a substrate. It may take some time for cells as an subject to adhere and thus the cells may be free floating for a certain period of time even in adherent culture, but the culture is defined to be an adherent culture as long as the cells finally adhere to a substrate, how long it may take. The medium used for suspension culture is not particularly limited and examples include DMEM and F12. It is, however, preferable to use a medium supplemented with serum (e.g., FBS), N2, B27 and/or an extrinsic factor such as a growth factor, and it is most preferable to use DMEM/F12 as this medium. The extrinsic factor to be added may include at least one growth factor selected from the group consisting of bFGF, EGF, IGF1, Wnt3a, FGF9, FGF20, heparin, and a TGFβ inhibitor. It is, however, preferable that the medim contains a growth factor and heparin, and it is more preferable that the medium contains all of the growth factors indicated just above. Preferable concentrations of them are 10 to 50, 10 to 50, 10 to 100, 10 to 50, 10 to 100, 10 to 100, 1 to 50 ng/ml, respectively, but are not particularly limited. The cells are cultured in suspension preferably for 3 to 7 days, more preferably for 4 to 6 days, and most preferably for 5 days.

Subsequently, the cells are further cultured in suspension after the addition of medium, preferably for 3 to 7 days, more preferably for 4 to 6 days, and most preferably for 5 days. The medium to be added is not particularly limited and examples include DMEM and F12. It is, however, preferable to use a medium supplemented with serum (e.g., FBS), N2, B27 and/or an extrinsic factor such as a growth factor, and it is most preferable to use DMEM/F12 as this medium. It is preferable to use the medium identical to the one used for the initial suspension culture except for the extrinsic factor. The extrinsic factor to be added may include at least one growth factor selected from the group consisting of bFGF, EGF, and IGF1, but it is preferable that the medium contains all of them. Preferable concentrations of them are 10 to 30 ng/ml, 10 to 30 ng/ml, and 10 to 50 ng/ml, respectively.

The spheres formed are then collected not so as to be broken and they are cultured adherently on a substrate using the same medium. After 1 hour to 2 days, preferably after 1 hour to 36 hours, most preferably on the following day, the medium is replaced with a fresh medium containing serum (e.g., FBS), N2, B27, and an extrinsic factor such as a growth factor. The extrinsic factor to be added is preferably T3 and/or IGF1. It is preferable to use the medium identical to the one used for the initial suspension culture except for the extrinsic factor. Their preferable concentrations are 10 to 100 and 1 to 50 ng/ml, respectively. Hair cells, supporting cells, cochlear ganglion cells and stria vascularis cells can be allowed to differentiate by further culturing the cells preferably for 3 days or longer, and more preferably for 5 days or longer. During this culture, exchange of the media may be the only thing to do.

[3] Induction of Differentiation of Inner Ear Stem Cells Into Cochlear Fibrocytes, Stria Vascularis Cells, and Pendrin-Positive Cells Via Periotic Mesenchymal Cells A induction method from inner ear stem cells to periotic mesenchymal cells include the step of culturing inner ear stem cells in a medium containing bFGF. Other steps not essential for the present invention can be added to this method.

The medium used here is not particularly limited and examples include DMEM and F12. It is, however, preferable to use a medium supplemented with serum (e.g., FBS) and bFGF, and it is more preferable to use DMEM as this medium. A preferable concentration of bFGF is 1 to 50 ng/ml. The cells are cultured preferably for 7 days or longer, more preferably for 10 days or longer, and most preferably 14 days or longer. After this culture, periotic mesenchymal cells having fibrous structures are obtained.

Cochlear fibrocytes and stria vascularis cells are obtained by further culturing the cells in a fresh medium without bFGF preferably for 7 days or longer, more preferably for 10 days or longer, and most preferably for 14 days or longer.

Pendrin-positive cells are obtained by further culturing the cells in a fresh medium without bFGF but with $NaHCO_3$ added preferably for 7 days or longer, more preferably for 10 days or longer, and most preferably for 14 days or longer. A preferable concentration of $NaHCO_3$ is 0.3% to 1%.

(5) Use of Apoptosis Inhibitor

The apoptosis inhibitors described in (1) can be used either in vivo or in vitro.

When an apoptosis inhibitor is used in vivo, it can be formulated as described below depending on the route of administration.

In addition to an active ingredient, various components that are typically used can be contained, if necessary. For example, one or more pharmaceutically acceptable vehicles, disintegrators, diluents, lubricants, flavoring agents, colorants, sweeteners, taste masking agents, suspending agents, wetting agents, emulsifiers, dispersing agents, auxiliary agents, antiseptics, buffers, binders, stabilizers, and coating agents can be contained.

As a route of administration, either of systemic administration and topical administration can be selected. Specifically, an appropriate route of administration is selected depending on the disease, symptom, etc. The pharmaceutical agents according to the present invention can be administered either orally or parenterally, but oral administration is preferred. Examples of parenteral administrations include subcutaneous, intradermal, intramuscular, and intratympanic administrations other than typical intravenous and intraarterial administrations. Furthermore, transmucosal or transdermal administration can be used.

The dosage form is not particularly limited and various dosage forms such as, for oral administration as an example, tablets, capsules, powders, granules, pills, liquids, emulsions, suspensions, solutions, spirits, syrups, extracts, or elixirs can be used. For parenteral agents, examples include injections such as subcutaneous injections, intravenous injections, intramuscular injections, and intraperitoneal injections; transdermal therapeutic systems or patches, ointments or lotions; sublingual preparations and oral patches for buccal administration; aerosols for nasal administration; and suppositories, but are not limited thereto. These formulated agents can be produced by known methods commonly used in a process of producing formulated agents. The pharmaceutical agents according to the present invention may be in a sustained or sustained release dosage form.

The amount of the active ingredient contained in the pharmaceutical agent can appropriately be determined depending on, for example, a dose range for the active ingredient and the number of administrations.

The dose range is not particularly limited and is appropriately selected depending on, for example, efficacy of ingredient(s), administration process, a route of administration, the type of disease, information associated with a subject (such as body weight, age, medical condition and use of other medicaments, etc.), and a decision of an attending physician. Generally, a suitable dose is, for example, around 100 mg to 3000 mg, preferably about 2250 mg or less, more preferably about 750 mg or less per adult per day, and about 100 mg to 2000 mg, preferably about 1500 mg or less, more preferably about 750 mg or less per child per day. These doses can, however, be modified using conventional routine experiments for optimization well known in the art. The above dose can be administered once a day to several times a day.

On the other hand, apoptosis of inner ear cells can be inhibited in vitro by adding an apoptosis inhibitor to a medium used for cell culture and using that medium for culturing the inner ear cells. The concentration of the apoptosis inhibitor to be added to the medium is not particularly limited but is preferably 0.1 nM to 1.0 nM for rapamycin derivatives and 1 mM to 10 mM for biguanide compounds.

(6) Method of Treating Inner Ear Hearing Impairment Resulted from Apoptosis

A method of treating inner ear hearing impairment resulted from apoptosis according to the present invention includes the step of administering a biguanide compound and/or a rapamycin derivative to a patient suffered from inner ear hearing impairment resulted from apoptosis. The biguanide compound and the rapamycin derivative are as described in (2) and (3). The biguanide compound or the rapamycin derivative can be administered by the method using the apoptosis inhibitor in vivo as described in (5).

(7) Method of Examining Apoptosis

A method of examining apoptosis according to the present invention includes the steps of administering a biguanide compound and/or a rapamycin derivative in vitro to an inner ear cell, inducing apoptosis in the inner ear cell; and examining the apoptosis induced in the inner ear cell. The biguanide compound and the rapamycin derivative are as described in (2) and (3).

The biguanide compound may be a lead compound synthesized from metformin or rapamycin used as a seed compound, and the rapamycin derivative may be a lead compound synthesized from rapamycin used as a seed compound.

The inner ear cells used here are as described in (1).

As the method of inducing apoptosis in the inner ear cells, a known method can be used and examples include a treatment with epoxomicin (e.g., treatment with 0.5 µM of epoxomicin for 24 hours).

As the method of examining the apoptosis thus induced in the inner ear cells, a known method can be used and examples include a method of detecting, using Annexin V, phosphatidylserine that has removed to the outside of the cell membrane as a result of apoptosis, a method of detecting the phenomenon that the cell membrane has permeated 7-AAD (7-amino-actinomycin D), a method of detecting activated caspase with a fluorescently labeled caspase inhibitor, SR-VAD-FMK (sulforhodamine-valyl-alanyl-aspartyl-fluoromethylketone), and a method of detecting fragmented DNA.

(8) Method of Screening Compounds for an Apoptosis Inhibitor

A method of screening biguanide compounds for an apoptosis inhibitor according to the present invention includes the steps of administering biguanide compounds represented by the following structural formula, which are candidates for an apoptosis inhibitor, to inner ear cells in vitro; inducing apoptosis in the inner ear cells; and examining the apoptosis induced in the inner ear cells. Details of these steps are as described in (5) and (7).

In parallel with these steps, apoptosis is induced in the same inner ear cells as above without administration of the aforementioned compounds and the resultant apoptosis is examined. Ratios of the cells undergoing apoptosis are compared between the groups with and without the administration of the compounds. The compounds that have caused inhibition of apoptosis are identified as apoptosis inhibitors.

(9) Method of Screening Compounds for a Pharmaceutical Agent for Treating Inner Ear Hearing Impairment Resulted from Apoptosis A method of screening biguanide compounds for a pharmaceutical agent according to the present invention includes the steps of administering biguanide compounds represented by the following structural formula, which are candidates for a pharmaceutical agent, to inner ear cells in vitro; inducing apoptosis in the inner ear cells; and examining the apoptosis induced in the inner ear cells. Details of these steps are as described in (5) and (7). Apoptosis inhibitors are then identified and used as pharmaceutical agents for treating inner ear hearing impairment resulted from apoptosis. The method of identifying the apoptosis inhibitors is as described in (8).

EXAMPLES

In the following example, Pendred syndrome is described as an example of inner ear hearing impairment resulted from apoptosis but the inner ear hearing impairment is not limited to this disease.

(1) Induction of Differentiation of iPS Cells Derived from Patients with Pendred Syndrome Into Inner Ear Cells (1-1) Establishment of iPS Cells Derived From Patients with Pendred Syndrome For reprogramming, OCT3/41, SOX2, KLF4, LIN28, L-MYC, and a p53shRNA expression vectors were introduced into mononuclear cells isolated from peripheral blood of patients with Pendred syndrome. The details are described below.

Isolation of mononuclear cells from peripheral blood specimens from patients and transfection of expression vectors into the cells by electroporation were performed as follows. Approximately 8 ml of blood was put into a Vacutainer blood collection tube containing ACD solution (manufactured by BD) and mixed. Then an equivalent volume of PBS was added thereto and mixed. The blood/PBS mixture was layered over Ficoll whose volume is equal to the blood/PBS mixture. After centrifugation at 400 G for 30 minutes at 25° C., a white intermediate layer was collected slowly with a pipetman, to which 12 ml of PBS was added and the mixture was centrifuged at 200 G for 10 minutes at 25° C. After removing the supernatant by aspiration, an appropriate volume of KBM-502 was added to suspend the cells and the number of cells was counted. $3 \times 10^6$ cells were removed into each of 15-ml tubes and centrifuged at 200 g for 10 minutes at 25° C. After discarding the supernatant, the cells were suspended in a culture liquid containing a reprogramming factor expression vector, electroporated using a Nucleofector II Device, suspended in a blood cell culture medium KBM-502 containing CD34 antibody, and seeded onto mouse-derived feeder cells. As the reprogramming factor expression vector, a mixture of pCE-hOCT3/4 (0.63 μg), pCE-hSK (0.63 μg), pCE-hUL (0.63 μg), pCE-mp53DD (0.63 μg), and pCXB-EBNA1 (0.50 μg) was introduced into cells.

Colonies of iPS cells were obtained 3 weeks after the seeding onto the feeder-cells and iPS cell lines derived from each patient were established from a single colony. Their quality as iPS cells were confirmed by examining expressions of undifferentiation markers, ability to differentiate into the three germ layers, and karyotypes.

To examine expressions of undifferentiation markers, fluorescent antibody staining was performed by adding mouse OCT3/4 antibody, rabbit anti-NANOG antibody, rat anti-SSEA3 antibody, mouse anti-SSEA4 antibody, mouse anti-TRA1-60 antibody, mouse anti-TRA1-81 antibody (1:500, 1:1000, 1:300, 1:500, 1:500, and 1:500, respectively) after antigen retrieval to the fixed iPS cells and staining them with fluorescent-labeled secondary antibodies specific for IgG of respective animal species. The expressions were examined by observation under a fluorescence microscope.

Ability to differentiate into the three germ layers was examine as follows. The iPS cells cultured on feeder cells were separated from the feeder cells using a dissociation solution and then cultured in suspension for 1 week on low attachment plates (Corning Ultra-Low Attachment plate) to form embryoid bodies. One week later, the embryoid bodies formed were collected and seeded in wells coated with poly-O-fibronectine. The seeded embryoid bodies were cultured continuously for 3 weeks for differentiation. The ability to differentiate into the three germ layers was examined by fluorescent antibody staining 3 weeks after the seeding. For fluorescent antibody staining, mouse anti-β-3 tubulin antibody (an ectoderm marker), mouse anti-SMA antibody (a mesoderm marker), and mouse anti-AFP antibody (an endoderm marker) were added (1:250, 1:150, and 1:250) to the cells fixed on glass slides after antigen retrieval. Subsequently, they were stained with fluorescent secondary antibodies specific for IgG of respective animal species, and the expressions were examined by observation under a fluorescence microscope.

Karyotypes were determined by G-banding and all line was comfirmed to have a normal karyotype.

(1-2) Induction of Differentiation of iPS Cells Into Inner Ear Stem Cells

[Differentiation Induction Method]

Day 0

1) One well (6-well plate) was coated with Matri Gel.

2) Feeder-free human iPS cells at confluence were treated with actase and detached from dishes.

3) The cells were diluted with PBS, centrifuged, and collected.

4) The supernatant was discarded and the cells were suspended in mTeSR1 with the ROCK inhibitor (Y27632) (10 μmol/L).

5) Only cells dissociated into single cells were obtained using a nylon mesh, and the number of cells was counted using a hemocytometer.

6) mTeSR1 containing Y27632 was added to the wells coated with Matri Gel in 1).

7) Dissociated cells were added at $2.0 \times 10^4/cm^2$ per well.

Day 1

The medium was replaced with ROCK inhibitor-free mTeSR1.

Day 2

The medium was replaced with a serum-free medium (DMEM/F12+B27+N2+GlutaMax+Nonessential amino acid). After that, the medium was replaced daily until Day 4.

Day 5

The medium was replaced with a serum-free medium (DMEM/F12+B27+N2+GlutaMax+Nonessential amino acid supplemented with bFGF, FGF3, FGF10, FGF19 and BMP4 (25 ng/ml, 25 ng/ml, 25 ng/ml, 25 ng/ml, 10 ng/ml, respectively)). After that, the medium was replaced daily until Day 7.

Day 8

The medium was replaced with a serum-free medium (DMEM/F12+B27+N2+GlutaMax+Nonessential amino acid supplemented with bFGF, FGF3, FGF10, and FGF19 (25 ng/ml, 25 ng/ml, 25 ng/ml, and 25 ng/ml, respectively)). After that, the medium was replaced daily until Day 10.

Day 11

The medium was replaced with a fresh serum-free medium (DMEM/F12+B27+N2+GlutaMax+Nonessential amino acid supplemented with bFGF, FGF3, FGF10, and FGF19).

Day 12

The cells were treated with actase, centrifuged, collected, and suspended in a DMEM/F12+N2+B27 medium supplemented with bFGF, FGF3, FGF10, and FGF19 (25 ng/ml, 25 ng/ml, 25 ng/ml, and 25 ng/ml, respectively). Cells dissociated into single cells were collected using a nylon mesh, and seeded in wells coated with poly-O-fibronectine. The cells were cultured under a hypoxic condition ($O_2$ 4%, and $CO_2$ 5%). Thereafter, the medium was replaced with a DMEM/F12+N2+B27 medium+bFGF, EGF, IGF1 (20 ng/ml, 20 ng/ml, 50 ng/ml) and subcultured every 6 days or so.

The obtained inner ear stem cells were grown and the confluent dishes were photographed with a phase contrast microscope (FIG. 1A).

[Antibody Staining]

The cells obtained were subjected to fluorescent antibody staining using anti-PAX2 antibody, anti-PAX8 antibody, and anti-SOX2 antibody which are markers for inner ear stem cells. For fluorescent antibody staining, rabbit anti-PAX2 antibody, mouse anti-PAX8 antibody, and goat anti-SOX2 antibody were added (diluted 1:50, 1:100, and 1:100, respectively) to the fixed cells on glass slides after antigen retrieval. Subsequently, they were stained with fluorescent secondary antibodies specific for IgG of respective animal species, and observed using a fluorescence microscope. As positive controls, cell nuclei were stained with Hoechst.

[Results]

As shown in FIG. 1B, about 80% of the cells expressed the markers for inner ear stem cells, which indicates that this method of inducing differentiation into inner ear stem cells is highly efficient.

(1-3) Induction of Differentiation of Inner Ear Stem Cells Into Hair Cells, Supporting Cells, and Cochlear Ganglion Cells

[Differentiation Induction Method]

The inner ear stem cells obtained in (1-2) was treated with actase, detached from dishes, and collected by centrifugation. A DMEM/F12+N2+B27 medium supplemented with bFGF, EGF, IGF1, Wnt3a, FGF9, FGF20, and Heparin (plus TGFβ inhibitor) (the concentrations of the factors were 25 ng/ml, 25 ng/ml, 50 ng/ml, 20 ng/ml, 50 ng/ml, 50 ng/ml, and 10 ng/ml, respectively) was added and cells were cultured in suspension on a low attachment plate (Corning Ultra-Low Attachment plate) (about 20,000 cells/well (96 well). One day later, formation of spheres began to be observed. On the fifth day of suspension culture, an equal volume of medium DMEM/F12+N2+B2 supplemented with bFGF, EGF, and IGF1 (the concentrations of the factors were 25 ng/ml, 25 ng/ml, and 50 ng/ml, respectively) was added.

On the tenth day of the suspension culture, the spheres were collected not so as to be broken, transferred to plates coated with poly-O-fibronectine, and cultured adherently on the plates (around 5-10 spheres/plate). On the following day, the medium was replaced with a DMEM/F12+N2+B27 medium supplemented with T3 and IGF1 (the concentrations of the factors were 60 ng/ml and 10 ng/ml, respectively), following which the medium was replaced every three days. On the fifth day of the adherent culture and later, hair cells, supporting cells, and cochlear ganglion cells were obtained.

[Antibody Staining]

For fluorescent antibody staining, rabbit anti-myosin VIIa antibody, mouse anti-espin antibody, and goat anti-prestin antibody were added (diluted 1:200, 1:100, and 1:50, respectively) to the fixed cells on glass slides after antigen retrieval. Subsequently, they were stained with fluorescent secondary antibodies specific for IgG of respective animal species, and observed under a fluorescence microscope.

Figure 2:
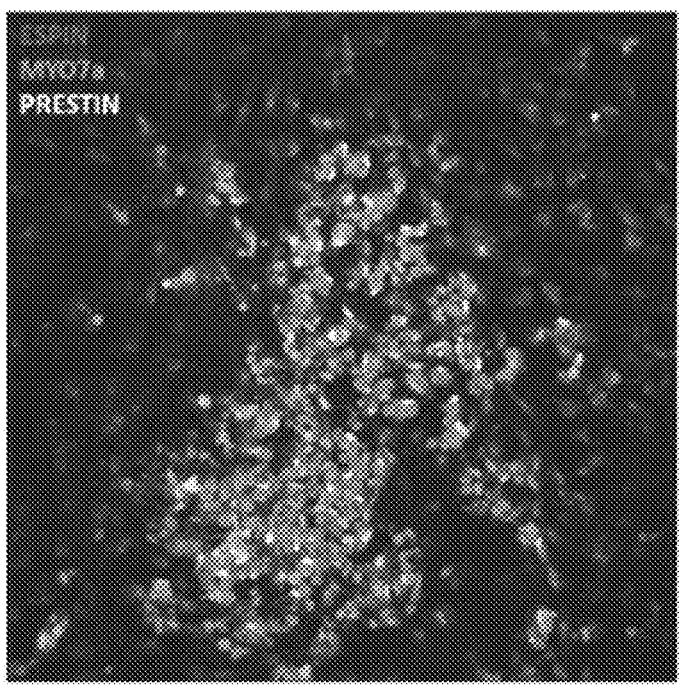
FIG. 2 Micrographs showing that espin, myosin VIa, and prestin, which are markers for hair cells, are expressed by culturing the inner ear stem cells in suspension and then culturing them in the presence of FGF 9 and FGF20 in one example of the present invention (Induction of differentiation into hair cells). The cells were stained with antibodies against espin, myosin VIa, and prestin (left; triple staining), an antibody against myosin VIa (upper right), and an antibody against espin (lower right).
Figure 2:
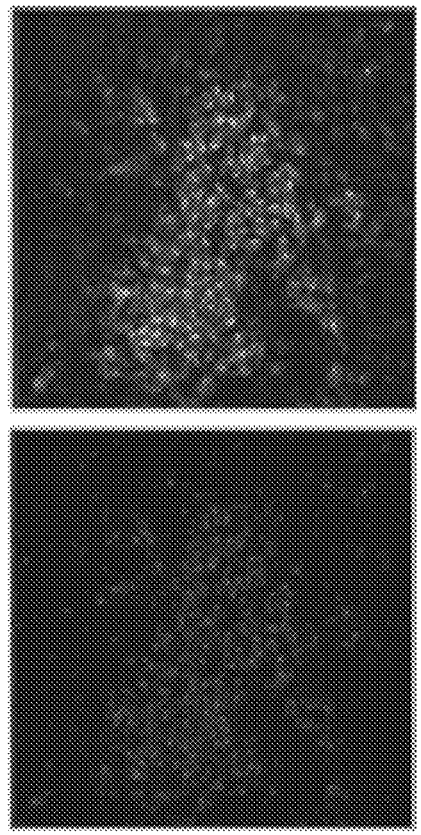
Figure 3:
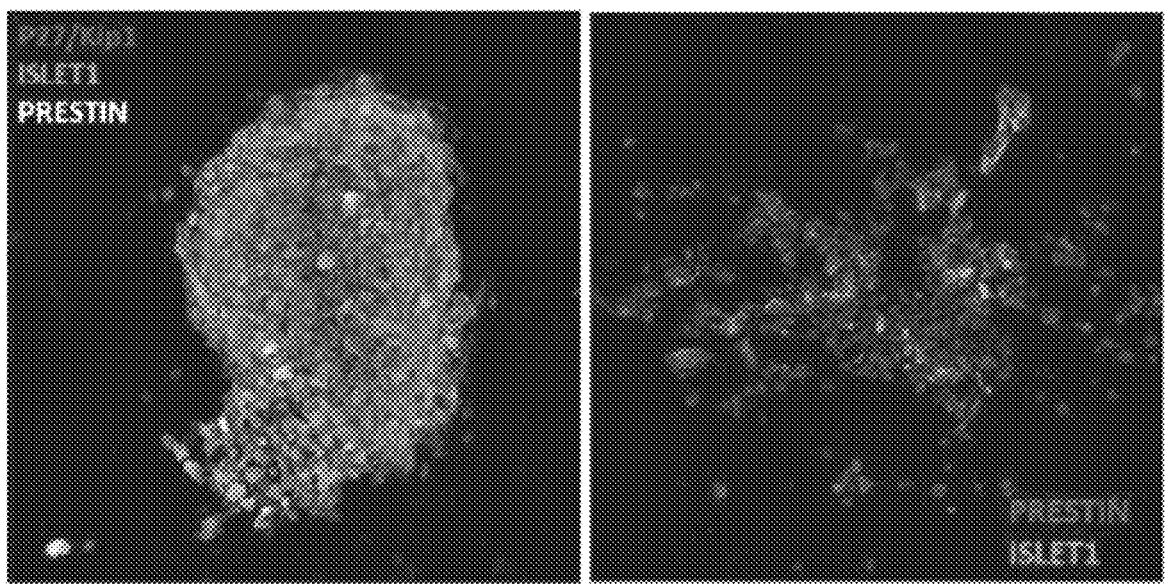
FIG. 3 Micrographs showing that p27kip1 and ISLET1, which are markers for supporting cells, are expressed by culturing the inner ear stem cells in suspension and then culturing them in the presence of FGF 9 and FGF20 in one example of the present invention (Induction of differentiation into supporting cells). The cells were stained with antibodies against p27kip1, ISLET1, and prestin (left; triple staining), and antibodies against ISLET1 and prestin (right; double staining).
Figure 4:
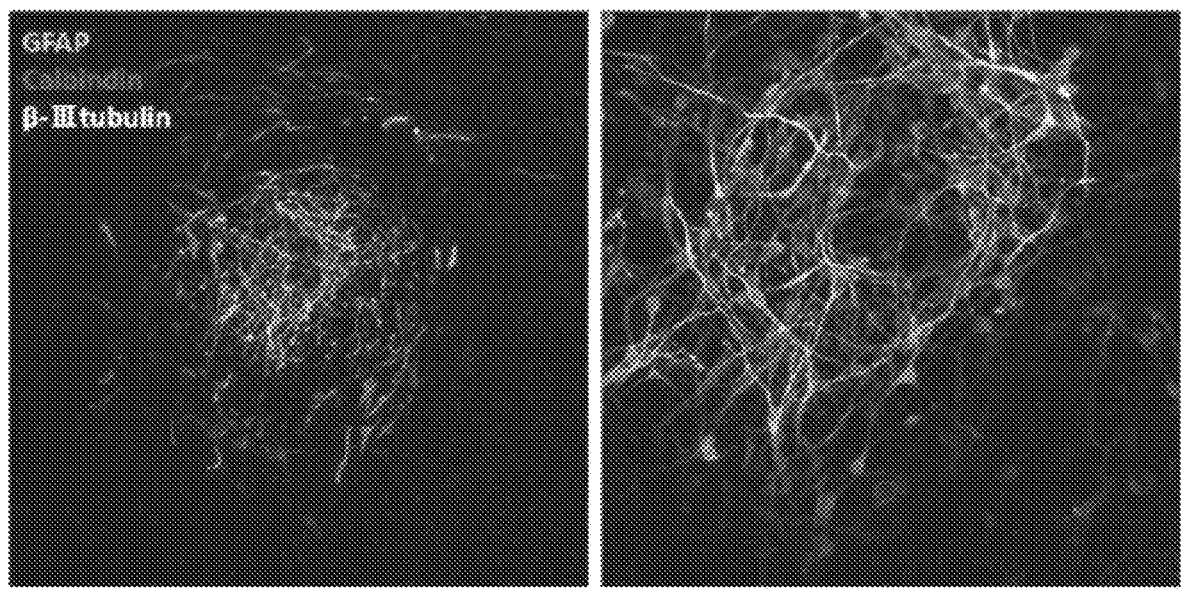
FIG. 4 Micrographs showing that GFAP, which is a marker for spiral ganglion glial cells and calbindin and beta III tubulin, which are markers for mature neurons, are expressed by culturing inner ear stem cells in suspension and then culturing them in the presence of FGF 9 and FGF20 in one example of the present invention (inducing differentiation of cochlear ganglion cells). The cells were triple-stained with antibodies to GFAP, calbindin, and beta III tubulin, respectively.

The cells obtained were subjected to fluorescent antibody staining with antibodies to espin, myosin VIIa, and prestin, which are markers for hair cells (FIG. 2). The cells were also subjected to fluorescent antibody staining with antibodies to islet 1, which is a marker for neurons, and to p27/Kip1 and prestin, which are markers for hair cells (FIG. 3). Furthermore, the cells were subjected to fluorescent antibody staining with antibodies to GFAP, which is a marker for spiral ganglion glial cells and calbindin and beta III tubulin, which are markers for mature neurons (FIG. 4).

[Results]

As shown in FIGS. 2 and 3, it was confirmed that differentiation of cells positive for myosin VIIa, espin, and prestin, which are markers for hair cells, and cells expressing p27kip1 or ISLET1, which are markers for supporting cells, were induced. Furthermore, as shown in FIG. 4, cells positive for calbindin, which is a marker for cochlear neurons, and their associated cells expressing GFAP, which glia cells express, were obtained. Thus, in this method, hair cells, supporting cells, and cochlear ganglion cells, which are the major cells constituting the inner ear sensory epithelial cells, are induced in three-dimensional constructs similar in topology to cells in living bodies.

Figure 5:
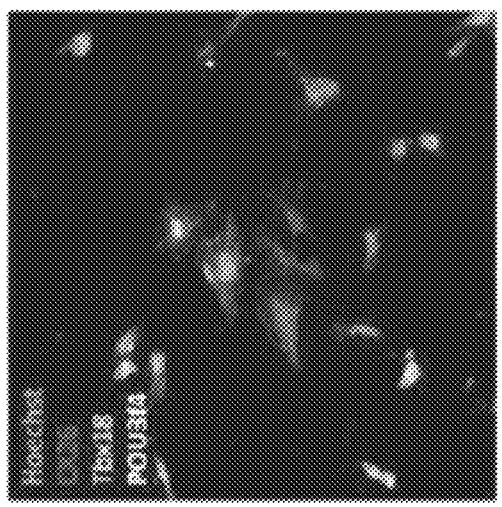
FIG. 5 Micrographs showing that S100, POU3F4, caldesmon, and TBX18, which are markers for periotic mesenchymal cells, are expressed by culturing the inner ear stem cells in the presence of bFGF in one example of the present invention (Induction of differentiation into periotic mesenchymal cells). The cells were triple-stained with antibodies against S100, caldesmon, and TBX18 (upper left), and antibodies against cx26, TBX18, and POU3f4 (upper right). Lower photos are phase contrast micrographs obtained after the cells were cultured for a long time in the presence of bFGF.
Figure 5:
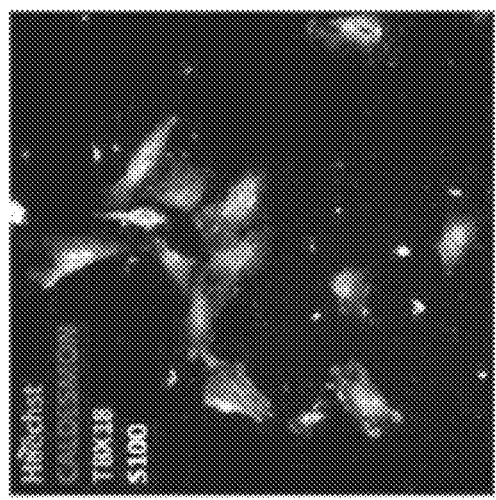
Figure 5:
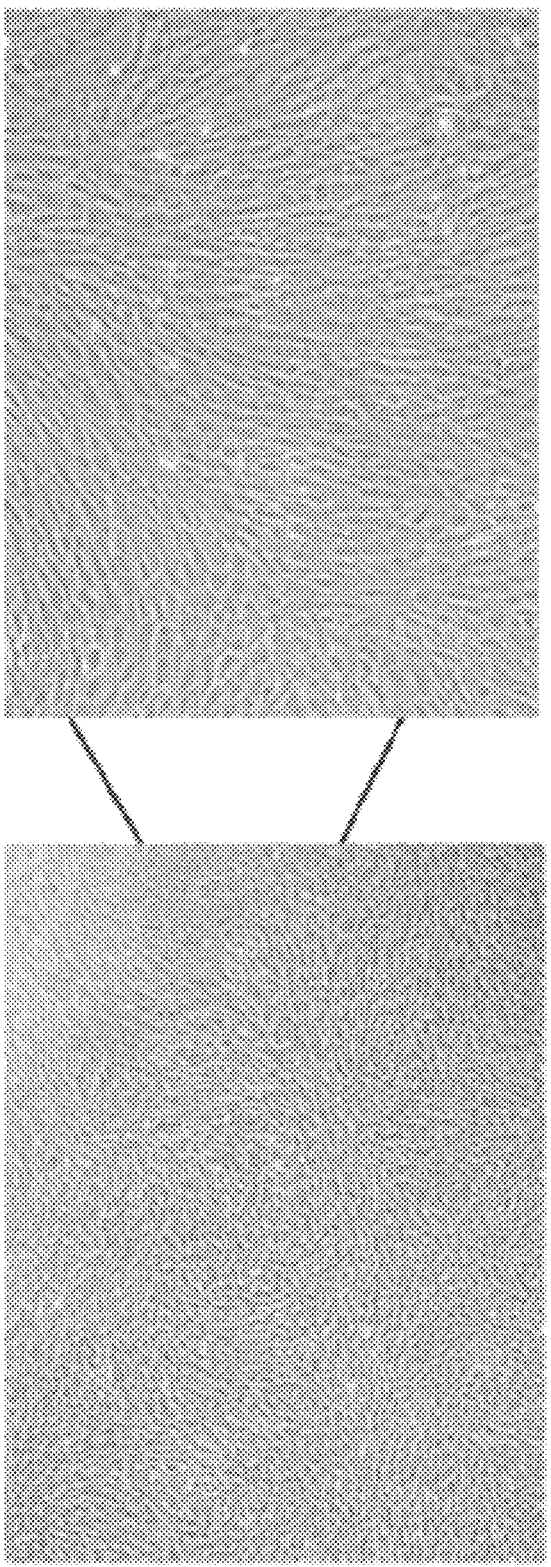

(1-4) Induction of Differentiation of Periotic Mesenchymal Cells, Cochlear Fibrocytes and Stria Vascularis, and Pendrin-Positive Cells The medium of the inner ear stem cells obtained in (1-2) was replaced with a POMC medium (DMEM 500 ml (D5796), 1 M HEPES 5 ml, FBS 30 ml, and bFGF (10 ng/ml) 2.0 ml) and the cells were cultured under a normal oxygen condition. Periotic mesenchymal cells were observed from around the tenth day of culture. Continuous culture resulted in fibrocyte-like structures after 2 weeks (FIG. 5).

The medium of the cells with the fibrocyte-like structures was replaced with DMEM containing 10% FBS and the cells were cultured for additional two weeks or so. Cochlear fibrocytes and stria vascularis cells were then obtained (FIG. 6).

Figure 6:
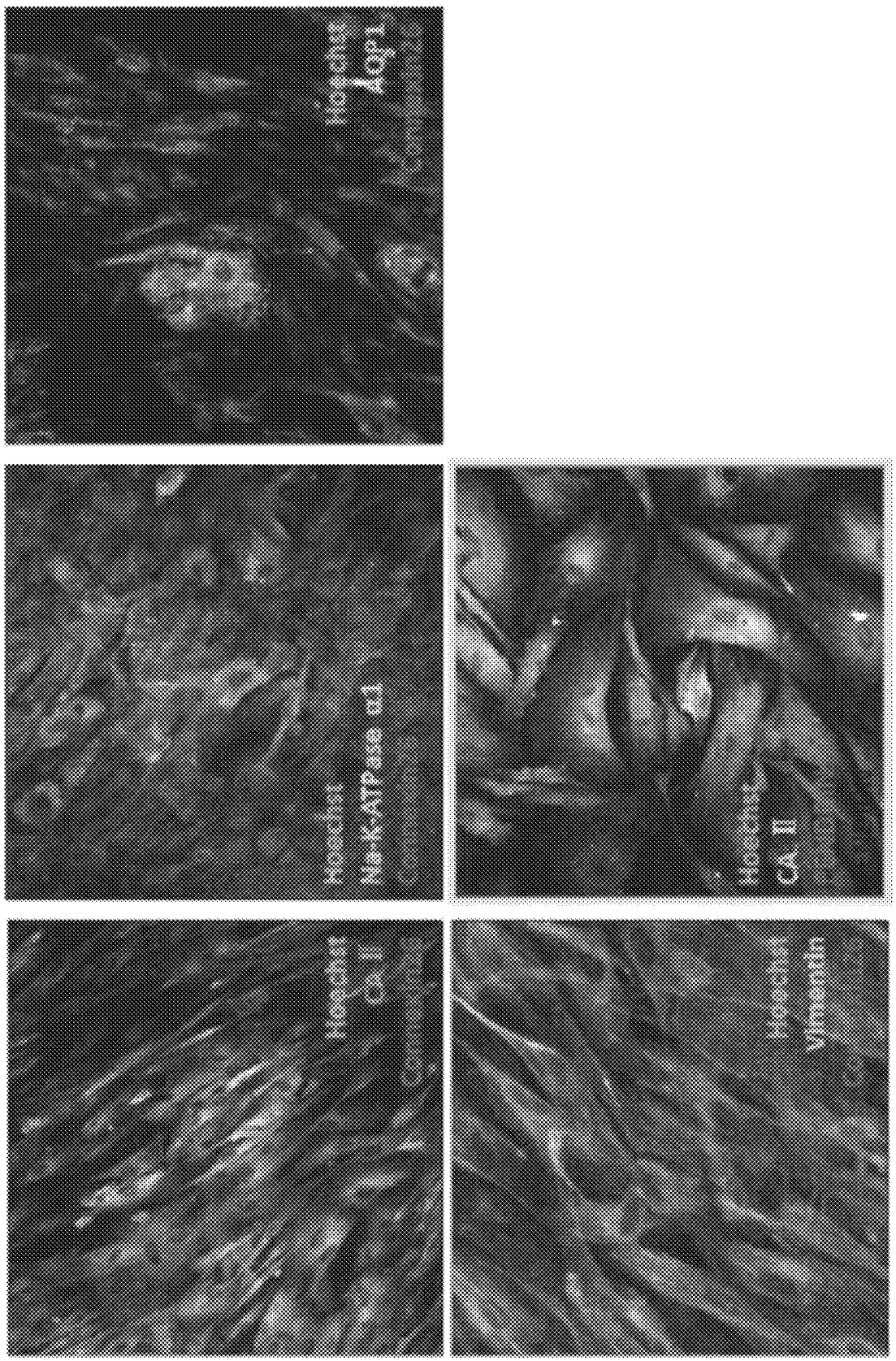
FIG. 6 Micrographs showing that carbonic anhydrase, aquaporin 1, sodium potassium ATPase, vimentin, connexins 26 and 30, which are markers for cochlear fibrocytes and stria vascularis cells of cochlear duct, are expressed by culturing the periotic mesenchymal cells in the presence of bFGF and then culturing them in the absence of bFGF, and that pendrin is expressed by culturing the periotic mesenchymal cells in the presence of bFGF and then culturing them in the presence of NaHCO₃ in one example of the present invention (Induction of differentiation into inner ear fibrocytes and pendrin-positive cells). The cells were double-stained with antibodies against CAII and connexin 26 (upper left), antibodies against sodium potassium ATPase and connexin 26 (upper middle), antibodies against aquaporin 1 and connexin 26 (upper right), and antibodies against vimentin and connexin 26 (lower left). The cells were double-stained with antibodies against CAII and pendrin (lower right).
Figure 7:
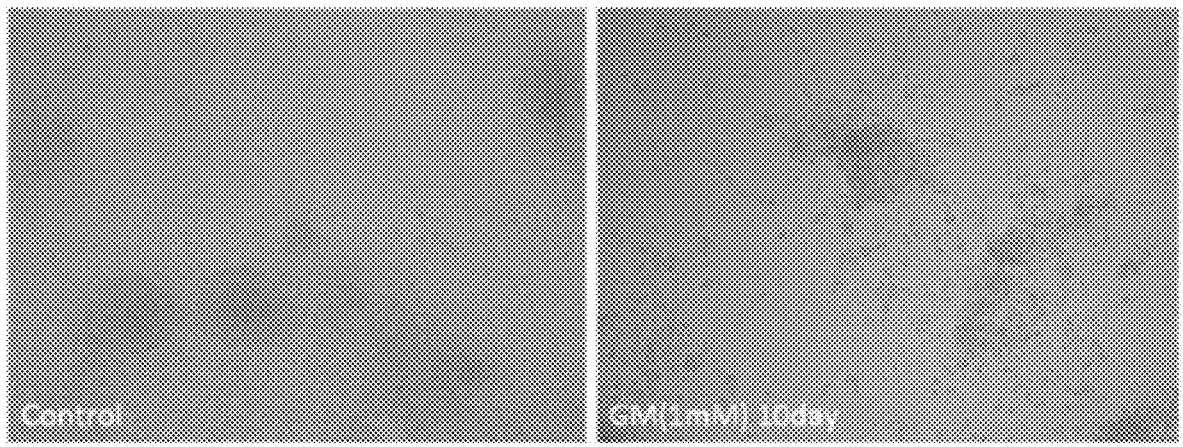
FIG. 7 Results indicating that damage of inner ear sensory epithelium was caused by administering gentamicin in one example of the present invention.
Figure 7:
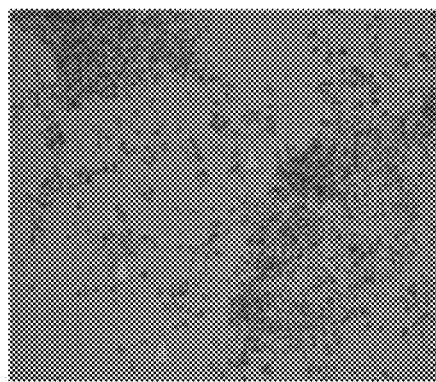

Pendrin-positive cells were also obtained by using DMEM containing 10% FBS supplemented with $NaHCO_3$ (0.375%) (FIG. 6).

[Antibody Staining]

For fluorescent antibody staining, rabbit anti-S100 antibody, POU3F4 antibody, mouse anti-caldesmon antibody, and goat anti-TBX18 antibody (diluted 1:3, 1:100, 1:100, and 1:50, respectively) were added to the fixed cells on glass slides after antigen retrieval. Subsequently, they were stained with fluorescent secondary antibodies specific for IgG of respective animal species, and observed under a fluorescence microscope As shown in FIG. 5, differentiation of the cells expressing S100, POU3F4, caldesmon, and TBX18, which are markers for periotic mesenchymal cells, were induced.

Following the cell induction using each induction method, rabbit anti-carbonic anhydraseII antibody, anti-aquaporin 1 antibody, anti-sodium potassium ATPase antibody, vimentin antibody, mouse anti-connexin 26 antibody, mouse anti-connexin 30 antibody, and goat anti-pendrin antibody were added (all of which were diluted 1:100) to the fixed cells on glass slides after antigen retrieval. Subsequently, they were stained with fluorescent secondary antibodies specific for IgG of respective animal species, and observed under a fluorescence microscope.

As shown in FIG. 6, carbonic anhydrase, aquaporin 1, sodium potassium ATPase, vimentin, connexins 26 and 30, which are expressed in cochlear fibrocytes and stria vascularis of cochlear duct, were expressed, it was concluded that these cells had been induced. Furthermore, since pendrin was expressed, it was concluded that pendrin-positive cells was induced.

(1-5) Administration of Gentamicin Known to Have Inner Ear Toxicity to Differentiation-Induced Inner Ear Sensory Epithelial Cells A gentamicin injection diluted 80 times was administered for 10 days to the inner ear sensory epithelial cells whose differentiation had been induced using this method. The number of cells was significantly decreased by administering the present pharmaceutical agent as compared with a control group, and it was shown that the cytotoxicity by the administration of gentamicin occurs in the same way as in a living body.

(2) Formation of Intracellular Aggregates in Inner Ear Cells Derived from iPS Cells of Patients with Pendred Syndrome

[Antibody Staining]

For fluorescent antibody staining, goat anti-pendrin antibody, mouse anti-ubiquitin antibody, and rabbit anti-LC3 antibody were added (diluted 1:100, 1:100, and 1:100, respectively) to the fixed cells on glass slides after antigen retrieval. Subsequently, they were stained with fluorescent secondary antibodies specific for IgG of respective animal species, and observed under a fluorescence microscope.

[Results]

Figure 8:
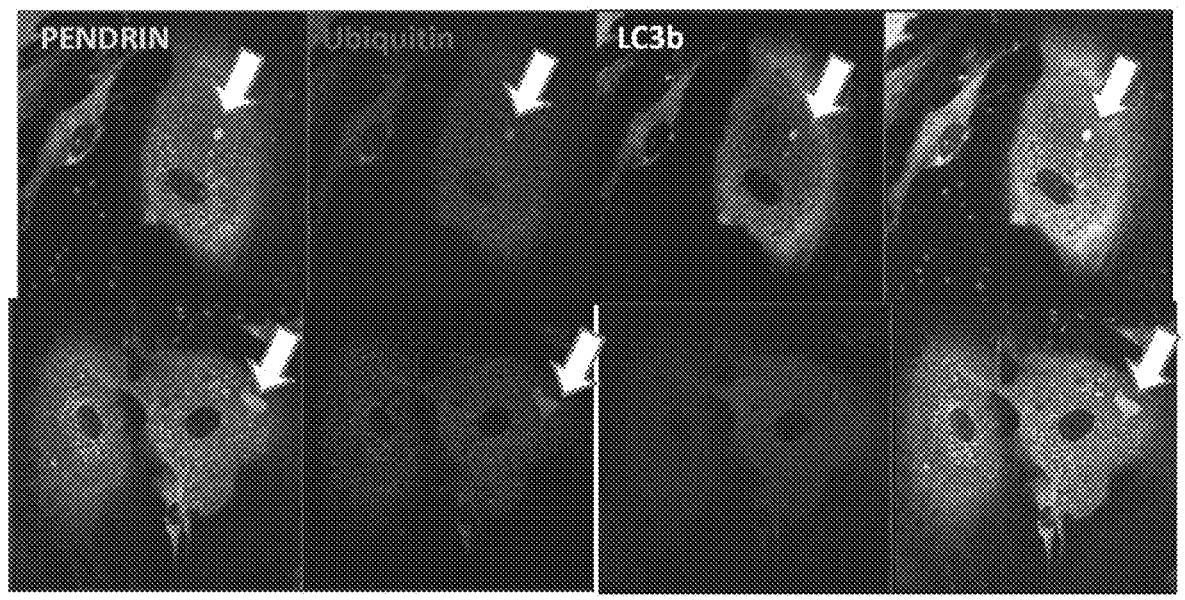
FIG. 8 Photographs showing that intracellular aggregates are formed in inner ear cells derived from iPS cells of patients with Pendred syndrome in one example of the present invention.

As shown in FIG. 8, in the inner ear cells derived from patients with Pendred syndrome, pendrin forms aggregates, in which ubiquitin and LC3b are present together. Thus, these intracellular aggregates are processed with both of the ubiquitin proteasome system and autophagy.

(3) Susceptibility of Inner Ear Cells Derived from iPS Cells of Patients with Pendred Syndrome to Stress

[Measurement of Cell Viability]

Pendrin-positive cells were induced from iPS cells derived from patients and iPS/ES cells derived from healthy subjects using the above method. The differentiation-induced cells were cultured in the presence of epoxomicin (0.5 µM) for 24 hours and then cellular stress was given to the cells.

For fluorescent antibody staining, goat anti-pendrin antibody and rabbit anti-Cleaved Caspase 3 antibody were added (diluted 1:100 and 1:300, respectively) to the fixed cells on glass slides after antigen retrieval. Cell nuclei were then stained with Hoechst 33258 (diluted 1:1000) and the cells were stained with fluorescent secondary antibodies specific for IgG of respective animal species. The resultant fluorescence was observed under a fluorescence microscope and the number of cells positive for pendrin but negative for Cleaved caspase 3 within the field of view was counted.

[Results]

Figure 9:
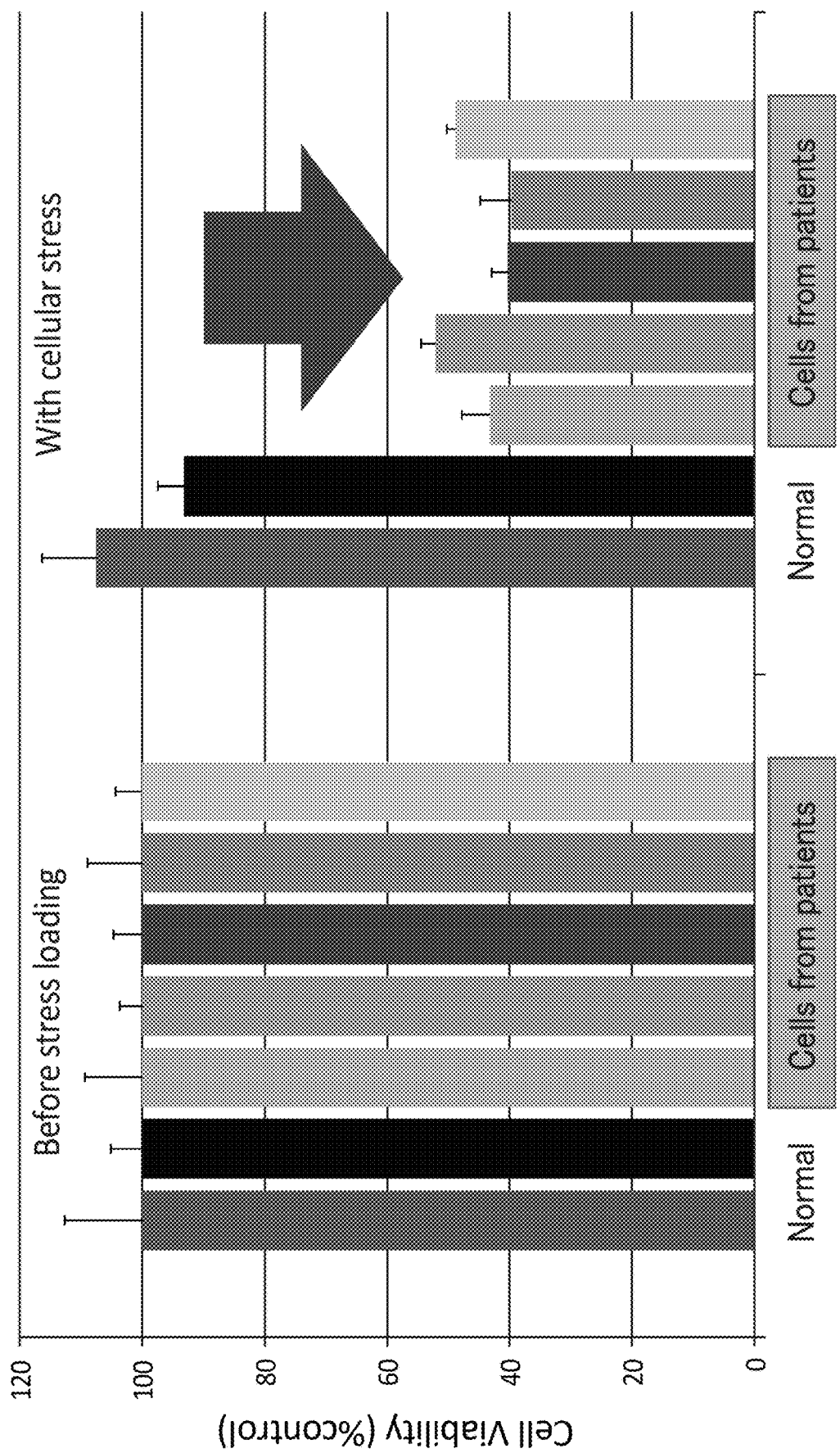
FIG. 9 Graph showing that viabilities of inner ear cells derived from iPS cells of a patient with Pendred syndrome are decreased when cells are stressed in one example of the present invention.

As shown in FIG. 9, the inner ear cells derived from patients with Pendred syndrome are more susceptible to stress and have lower cell viability under stress than normal cells.

(4) Suppression of the Decrease in the Cell Viability of the Aforementioned Inner Ear Cells with Rapamycin

[Measurement of Cell Viability]

Pendrin-positive cells were induced from iPS cells derived from patients and iPS/ES cells derived from healthy subjects using the above method. The differentiation-induced cells were subjected to the following treatment. In the rapamycin administration group, rapamycin was administered for 3 days. In the cellular stress/rapamycin group, rapamycin (0.2 nM) was administered for 2 days and then epoxomicin (0.5 µM) was administered as cellular stress for 24 hours along with rapamycin. In the cellular stress group, DMSO was administered for 2 days and then only epoxomicin (0.5 µM) was administered as cellular stress for 24 hours.

For fluorescent antibody staining, goat anti-pendrin antibody and rabbit anti-Cleaved Caspase 3 antibody were added (1:100 and 1:300, respectively) to the fixed cells on glass slides after antigen retrieval. Cell nuclei were then stained with Hoechst 33258 (diluted 1:1000). The cells were stained with fluorescent secondary antibodies specific for IgG of respective animal species and observed under a fluorescence microscope to count the number of cells positive for pendrin but negative for Cleaved caspase 3 within the field of view.

[Results]

Figure 10:
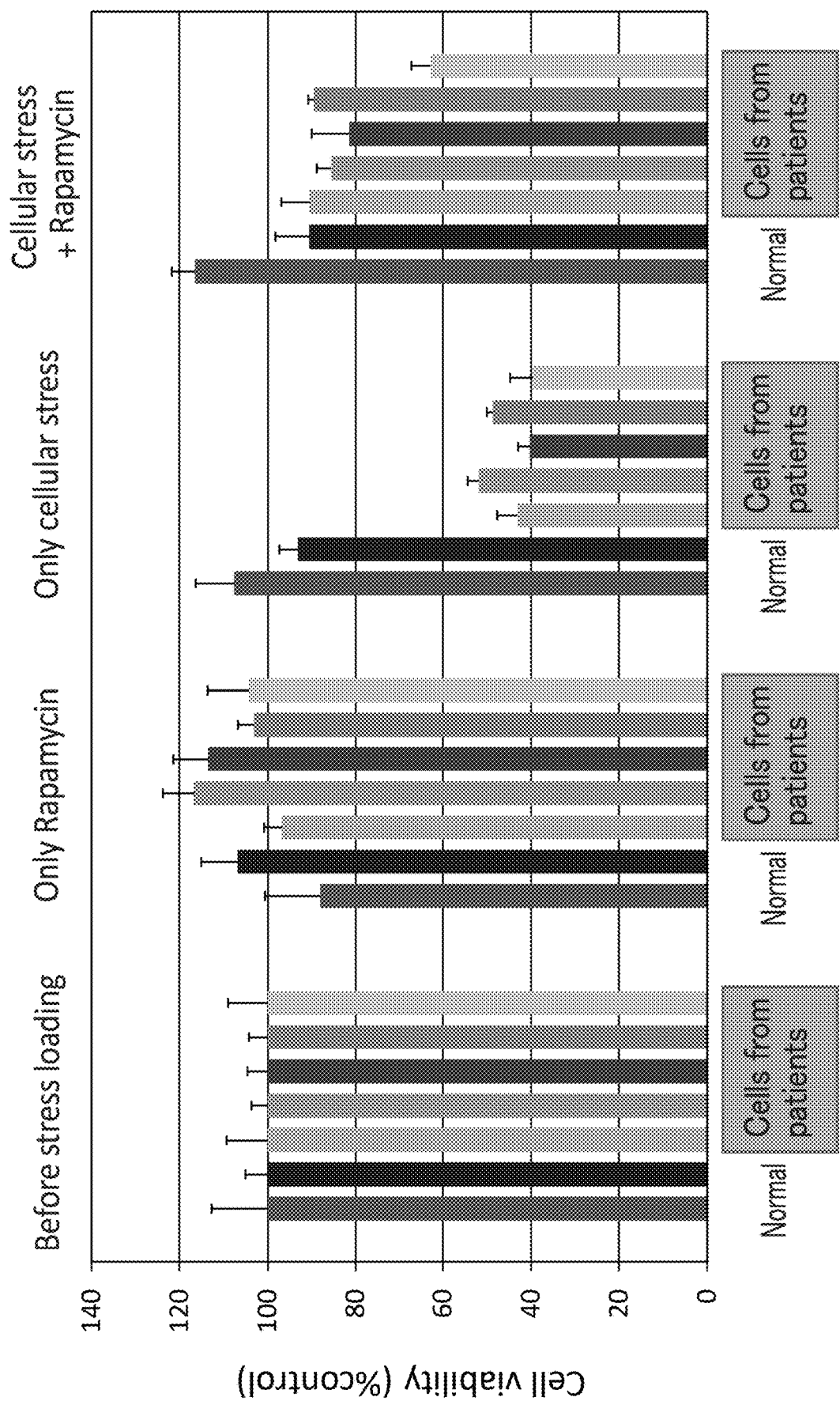
FIG. 10 Graph showing that rapamycin suppresses the decrease in cell viabilities shown in FIG. 9 in one example of the present invention.

As shown in FIG. 10, rapamycin suppresses decrease in cell viabilities when the inner ear cells derived from patients with Pendred syndrome are stressed.

(5) Inhibition of Apoptosis of the Aforementioned Inner Ear Cells with Rapamycin

[Measurement of Caspase 3-Positive Cells]

Pendrin-positive cells were induced from iPS cells derived from patients and iPS/ES cells derived from healthy subjects using the above method. The differentiation-induced cells were subjected to the following treatment. In the rapamycin administration group, rapamycin was administered for 3 days. In the cellular stress/rapamycin group, rapamycin (0.2 nM) was administered for 2 days and then epoxomicin (0.5 µM) was administered as cellular stress for 24 hours along with rapamycin. In the cellular stress group, DMSO was administered for 2 days and then only epoxomicin (0.5 µM) was administered as cellular stress for 24 hours.

For fluorescent antibody staining, goat anti-pendrin antibody and rabbit anti-Cleaved Caspase 3 antibody were added (1:100 and 1:300, respectively) to the fixed cells on glass slides after antigen retrieval. Cell nuclei were then stained with Hoechst 33258 (diluted 1:1000). The cells were stained with fluorescent secondary antibodies specific for IgG of responsive animal species and observed under a fluorescence microscope to count the number of cells positive for pendrin and Cleaved caspase 3 within the field of view.

[Results]

Figure 11:
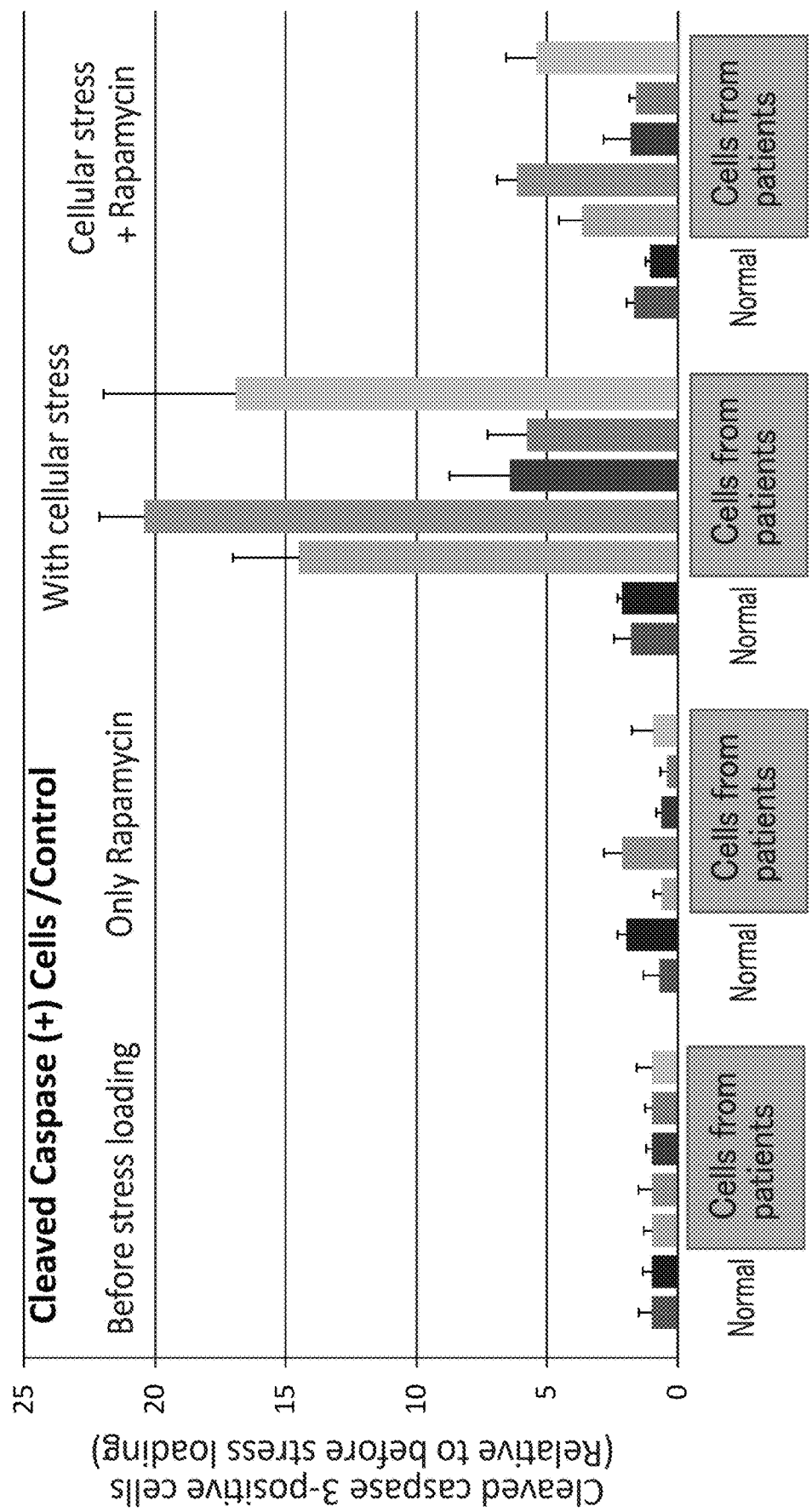
FIG. 11 Graph showing that rapamycin inhibits apoptosis which causes the decrease in cell viabilities shown in FIG. 9 in one example of the present invention.

As shown in FIG. 11, apoptosis is responsible for the decrease in cell viabilities when the inner ear cells derived from patients with Pendred syndrome are stressed, and rapamycin inhibits such apoptosis.

(6) Suppression of the Decrease in the Cell Viability of the Aforementioned Inner Ear Cells with Metformin

[Measurement of Cell Viabilities]

Pendrin-positive cells were induced from iPS cells derived from patients and iPS/ES cells derived from healthy subjects using the above method. The differentiation-induced cells were subjected to the following treatment. In the rapamycin administration group, rapamycin was administered for 3 days. In the cellular stress/rapamycin group, rapamycin (0.2 nM) was administered for 2 days and then epoxomicin (0.5 µM) was administered as cellular stress for 24 hours along with rapamycin. In the cellular stress group, DMSO was administered for 2 days and then only epoxomicin (0.5 µM) was administered as cellular stress for 24 hours. In the metformin administration group, 1 mM or 10 mM metformin was administered for 2 days and then epoxomicin (0.5 µM) was administered as cellular stress for 24 hours along with metformin. For fluorescent antibody staining, goat anti-pendrin antibody and rabbit anti-Cleaved Caspase 3 antibody were added (1:100 and 1:300, respectively) to the fixed cells on glass slides after antigen retrieval. Cell nuclei were then stained with Hoechst 33258 (diluted 1:1000). The cells were stained with fluorescent secondary antibodies specific for IgG of respective animal species and observed under a fluorescence microscope to count the number of cells positive for pendrin but negative for Cleaved caspase 3 within the field of view.

[Results]

Figure 12:
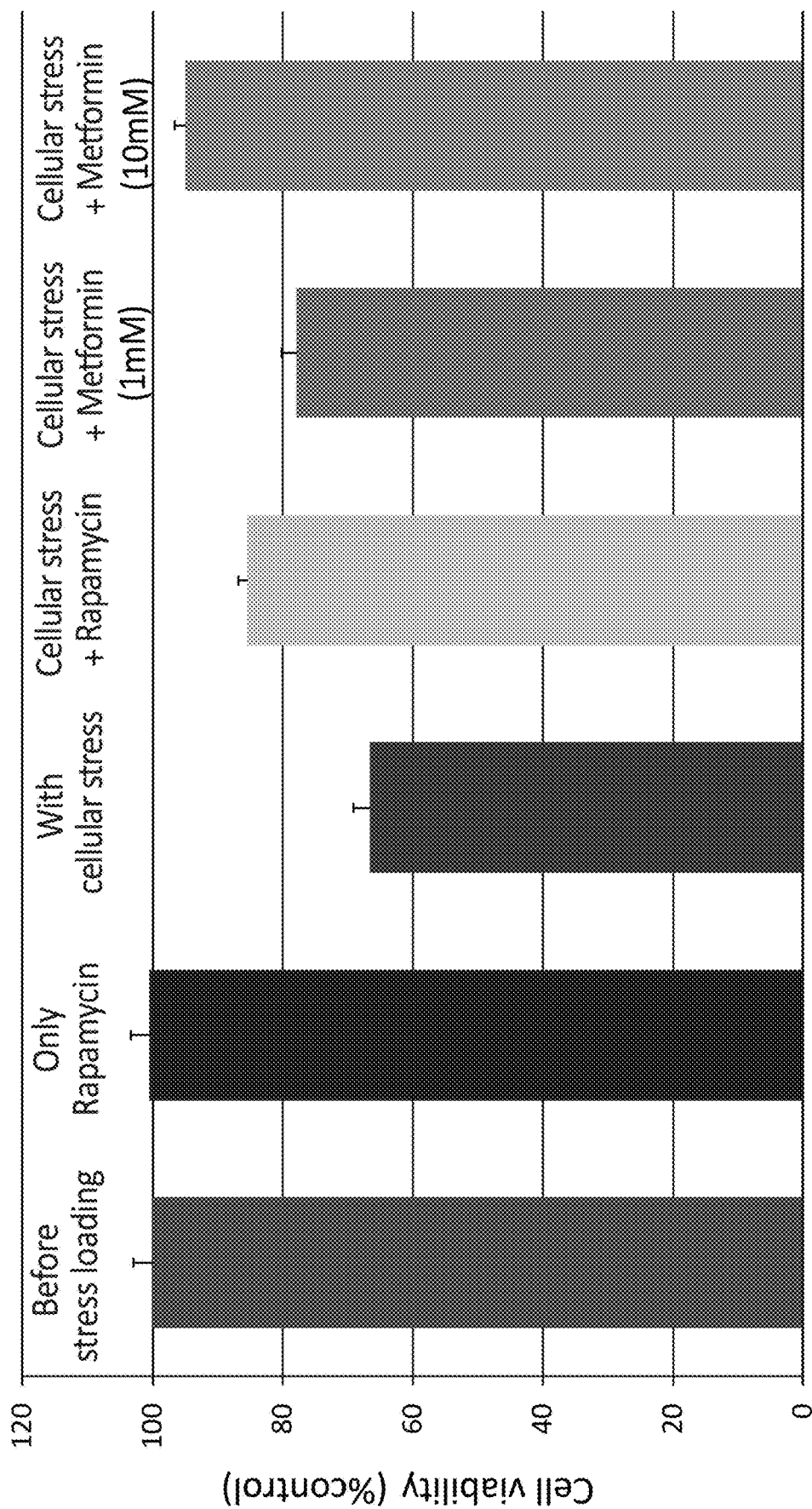
FIG. 12 Graph showing that metformin suppresses the decrease in cell viabilities shown in FIG. 9 in one example of the present invention.

As shown in FIG. 12, metformin suppresses the decrease in the cell viability when the inner ear cells derived from patients with Pendred syndrome are stressed.

(7) Inhibition of Apoptosis in the Aforementioned Inner Ear Cells with Metformin

[Measurement of Cell Viability]

Pendrin-positive cells were induced from iPS cells derived from patients and iPS/ES cells derived from healthy subjects using the above method. The differentiation-induced cells were subjected to the following. In the rapamycin administration group, rapamycin was administered for 3 days. In the cellular stress/rapamycin group, rapamycin (0.2 nM) was administered for 2 days and then epoxomicin (0.5 µM) was administered as cellular stress for 24 hours along with rapamycin. In the cellular stress group, DMSO was administered for 2 days and then only epoxomicin (0.5 µM) was administered as cellular stress for 24 hours. In the metformin administration group, 1 mM or 10 mM metformin was administered for 2 days and then epoxomicin (0.5 µM) was administered as cellular stress for 24 hours along with metformin. For fluorescent antibody staining, goat anti-pendrin antibody and rabbit anti-Cleaved Caspase 3 antibody were added (1:100 and 1:300, respectively) to the fixed cells on glass slides after antigen retrieval. Cell nuclei were then stained with Hoechst 33258 (diluted 1:1000). The cells were stained with fluorescent secondary antibodies specific for IgG of respective animal species and observed under a fluorescence microscope to count the number of cells positive for pendrin but negative for Cleaved caspase 3 within the field of view.

[Results]

Figure 13:
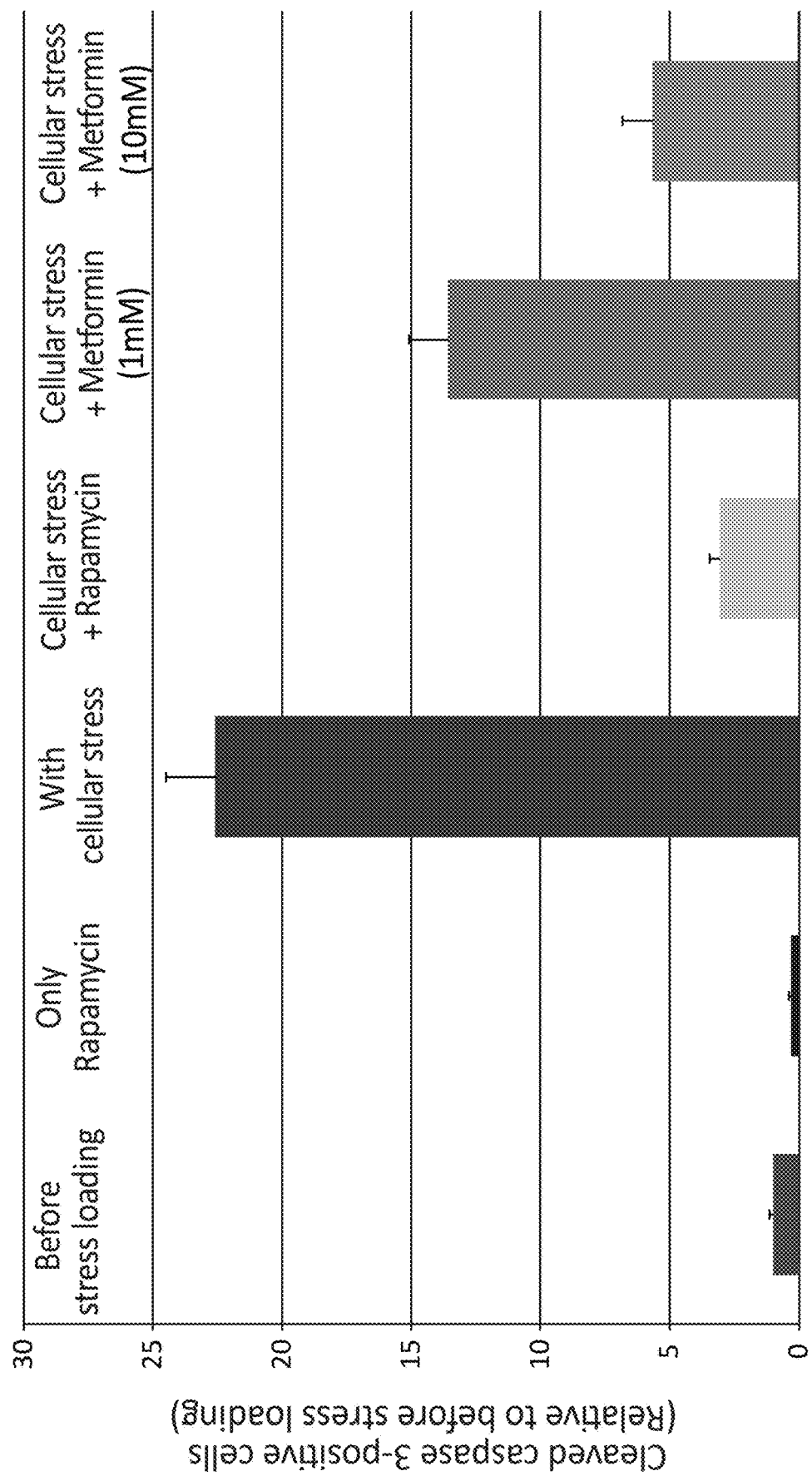
FIG. 13 Graph showing that metformin inhibits apoptosis which leads to decrease in cell viabilities shown in FIG. 9 in one example of the present invention.

As shown in FIG. 13, metformin inhibits apoptosis when the inner ear cells derived from patients with Pendred syndrome are stressed.

(8) [Reference Example] Calpeptin (the Following Structural Formula VI) Cannot Inhibit Apoptosis of the Aforementioned Inner Ear Cells

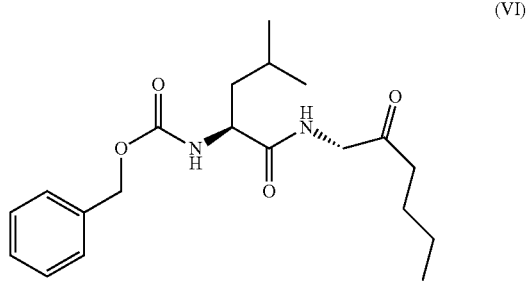

(VI)

[Measurement of Cell Viability]

Pendrin-positive cells were induced from iPS cells derived from patients and iPS/ES cells derived from healthy subjects using the above method. The differentiation-induced cells were subjected to the following treatment. In the calpeptin administration group, calpeptin was administered for 3 days. In the cellular stress/calpeptin group, calpeptin (0.5 nM) was administered for 2 days and then epoxomicin (0.5 µM) was administered as cellular stress for 24 hours along with calpeptin. In the cellular stress group, DMSO was administered for 2 days and then only epoxomicin (0.5 µM) was administered as cellular stress for 24 hours.

For fluorescent antibody staining, goat anti-pendrin antibody and rabbit anti-Cleaved Caspase 3 antibody were added (1:100 and 1:300, respectively) to the fixed cells on glass slides after antigen retrieval. Cell nuclei were then stained with Hoechst 33258 (diluted 1:1000). The cells were stained with fluorescent secondary antibodies specific for IgG of respective animal species and observed under a fluorescence microscope to count the number of cells positive for pendrin but negative for Cleaved caspase 3 within the field of view.

[Results]

Figure 14:
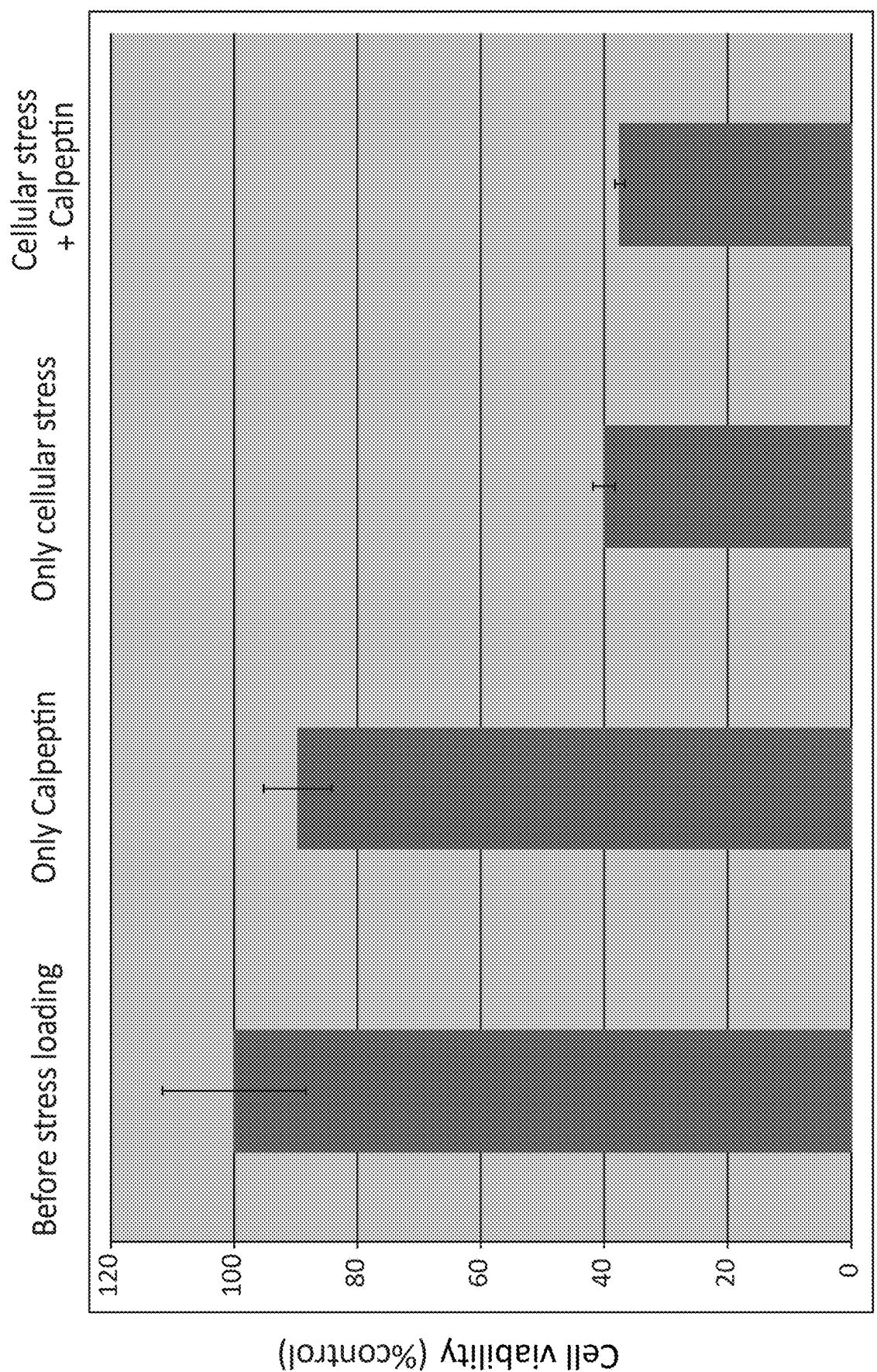
FIG. 14 Graph showing that calpeptin cannot inhibit apoptosis which leads to decrease in cell viabilities shown in FIG. 9 in one reference example of the present invention.

Calpeptin is a kind of calpain inhibitor. Although it is known to inhibit apoptosis of neurons in neurodegenerative diseases and the like, it cannot inhibit apoptosis in the inner ear cells derived from iPS cells of patients with Pendred syndrome, as shown in FIG. 14. This indicates that, even if a compound has an apoptosis inhibitory activity on cells other than inner ear cells, it is unclear whether the compound can inhibit apoptosis in inner ear cells.

INDUSTRIAL APPLICABILITY

The present invention made it possible to provide novel apoptosis inhibitors and therapeutic agents for inner ear hearing impairment.

The invention claimed is:

1. A method for treating a patient with inner ear hearing impairment caused by Pendred syndrome, wherein the patient possesses pendrin intracellular aggregates in an inner ear pendrin positive cell having a decrease in viability under cellular stress compared to a normal inner ear pendrin positive cell, the method comprising the step of administering an effective amount of a rapamycin derivative represented by the following formula II:

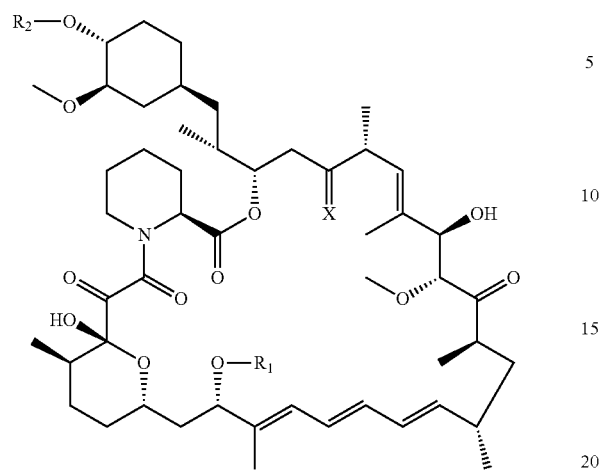
(II)
wherein $R_1$ is a $C_{1-6}$ alkyl or a $C_{3-6}$ alkynyl, $R_2$ is H, —CH2-OH or —CH$_2$—CH$_2$—OH, and X is =O, (H, H) or (H, OH) to suppress the decrease in the cell viability of the inner ear pendrin-positive cells due to cellular stress.
2. The method according to claim 1, wherein the rapamycin derivative is rapamycin.
\* \* \* \* \*